(12) United States Patent
Rudakov et al.

(10) Patent No.: US 11,974,755 B2
(45) Date of Patent: May 7, 2024

(54) OCCLUSIVE IMPLANT AND DELIVERY SYSTEM

(71) Applicant: ArtVentive Medical Group, Inc., San Marcos, CA (US)

(72) Inventors: Leon Rudakov, San Marcos, CA (US); Andy Black, Johnsburg, IL (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 190 days.

(21) Appl. No.: 17/190,380

(22) Filed: Mar. 2, 2021

(65) Prior Publication Data

US 2021/0267605 A1 Sep. 2, 2021

Related U.S. Application Data

(60) Provisional application No. 62/984,210, filed on Mar. 2, 2020.

(51) Int. Cl.
*A61B 17/12* (2006.01)
*A61F 2/88* (2006.01)

(52) U.S. Cl.
CPC .......... *A61B 17/12145* (2013.01); *A61F 2/88* (2013.01); *A61B 17/1204* (2013.01); *A61B 2017/12054* (2013.01); *A61F 2230/0013* (2013.01); *A61F 2230/0091* (2013.01)

(58) Field of Classification Search
CPC .......... A61B 17/1214; A61B 17/12145; A61B 2017/12054; A61B 17/221; A61B 17/0057; A61B 2017/00632; A61B 2017/00597; A61B 2017/00575; A61F 2/88; A61F 2/885; A61F 2230/0013; A61F 2230/0091; A61F 2/01; A61F 2/0105; A61F 2/0108; A61F 2002/016
See application file for complete search history.

(56) References Cited

U.S. PATENT DOCUMENTS

| | | | | |
|---|---|---|---|---|
| 5,133,732 | A * | 7/1992 | Wiktor | A61F 2/88 623/1.22 |
| 6,059,825 | A * | 5/2000 | Hobbs | A61F 2/0103 623/1.22 |
| 2002/0138094 | A1* | 9/2002 | Borillo | A61F 2/013 606/200 |
| 2002/0138129 | A1* | 9/2002 | Armstrong | A61F 2/07 623/1.11 |
| 2015/0245843 | A1* | 9/2015 | Theobald | A61B 17/12109 606/191 |

* cited by examiner

*Primary Examiner* — Kathleen S Holwerda
(74) *Attorney, Agent, or Firm* — Nathan S. Smith; Lauren C. Tittle; Morgan, Lewis & Bockius LLP

(57) ABSTRACT

An occlusive implant with a backbone support structure can be delivered into a body vessel using a delivery assembly that can engage with at least a portion of the implant. The assembly can utilize an engagement member and an engagement socket or a catheter or sheath to removably couple the engagement member with the implant. When the implant is advanced to a target location in the body vessel, the implant can be released to restrict flow of a fluid through the vessel and/or promote occlusion of the vessel.

21 Claims, 19 Drawing Sheets

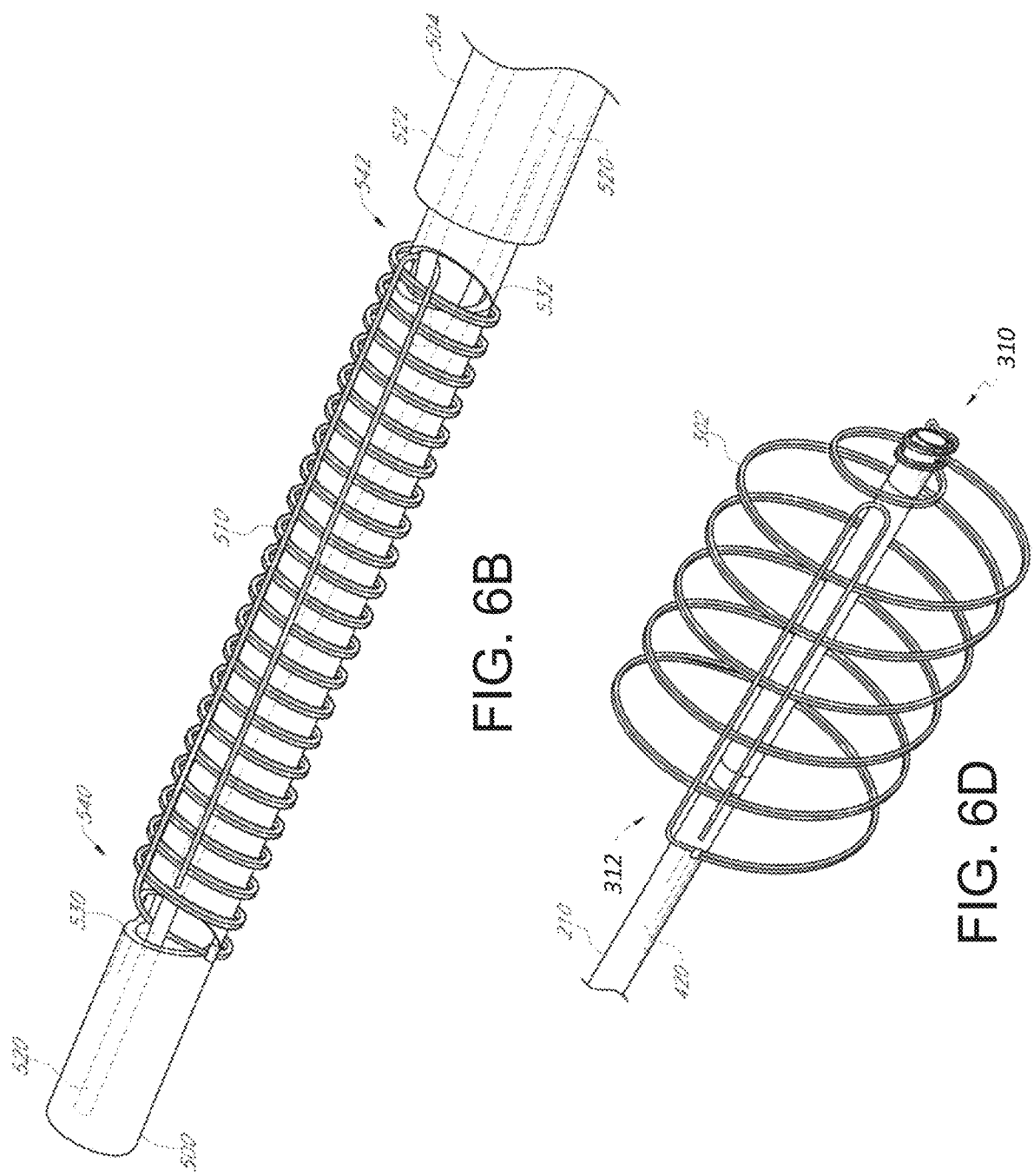

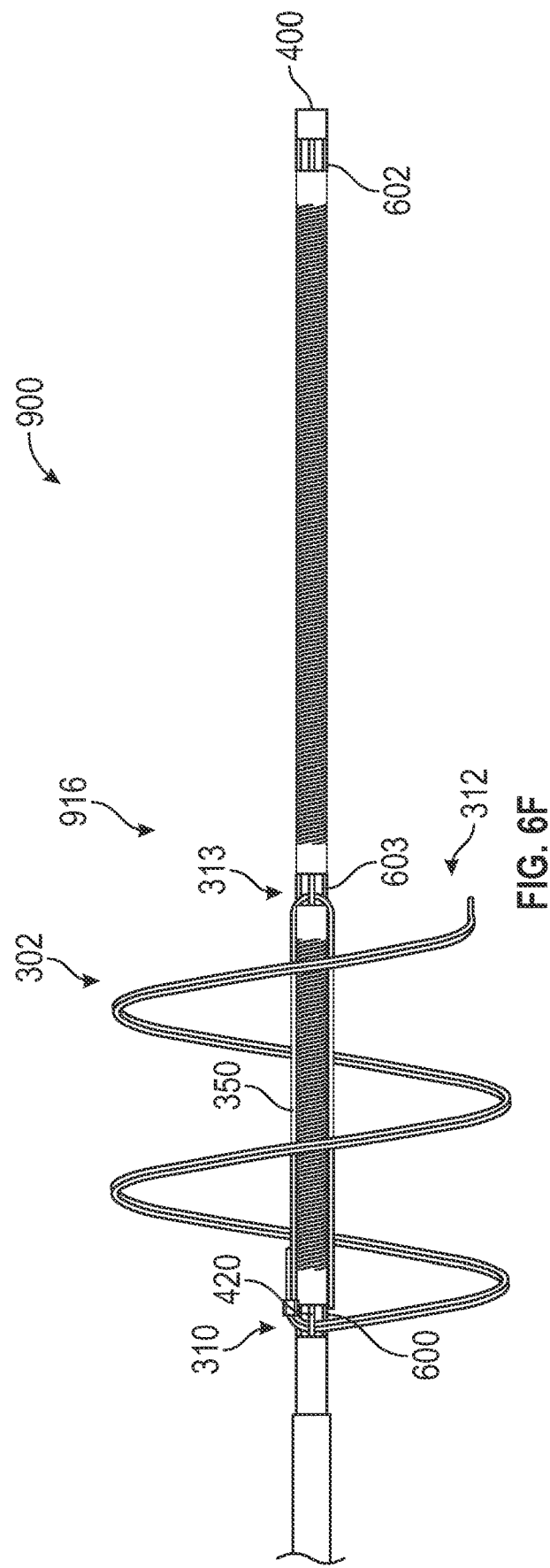

OCCLUSIVE IMPLANT AND DELIVERY SYSTEM

CROSS-REFERENCE TO RELATED APPLICATIONS

This application claims the benefit of and priority to U.S. Provisional Patent Application No. 62/984,210, filed on Mar. 2, 2020, the entirety of which is incorporated herein by reference.

FIELD

The subject technology relates generally to apparatuses and methods for blood vessel occlusion using an occlusive implant that has a minimal delivery profile, thereby allowing the implant to be delivered to small-diameter body lumens.

BACKGROUND

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms.

Typically made from latex or silicone, balloons are delivered to a desired location in a vessel, then inflated in order to physically occlude the vessel. While other devices have since been developed, balloon occlusion remains in use, and is indicated for use in treating a variety of life-threatening conditions, including for example, giant cerebral and skull base aneurysms, traumatic and non-traumatic vessel injury or rupture, vertebro-vertebral arteriovenous fistulas, and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency, intrahepatic arterioportal fistulas, treatment of varicoceles, shunt occlusion in patients with a Blalock-Taussig shunt, obliteration of pulmonary arteriovenous fistulas, arteriovenous malformations or aortopulmonary anastomoses, coronary arteriovenous fistulas, or renal arteriovenous fistulas. Detachable balloons are also used in preoperative devascularization before surgical resection of organs such as the kidney.

Additionally, despite the increase in system and implant options for occluding a body lumen, traditional devices and technology have been limited in their ability to reach small body lumens. Further, some implant options may utilize complex physical structures to mitigate implant migration issues, increasing manufacturing difficulty and cost. Accordingly, the present disclosure provides various delivery systems, engagement mechanisms, and implants that function to provide cost effective and immediate occlusion of a blood vessel as well as reliable, precise placement and minimal or no migration when the implant is released into the blood vessel.

SUMMARY

The present disclosure provides delivery systems, engagement mechanisms, and radially expandable implants, as wells as methods of achieving immediate vessel occlusion by delivery of the radially expandable implants. The immediate total occlusion of blood flow can be achieved using one or more occlusive components coupled to a frame of the implant.

Through use of the herein-disclosed delivery systems, engagement mechanisms, and implants, a clinician can achieve immediate occlusion of a blood vessel as well as reliable, precise placement and minimal or no migration when the implant is released into the blood vessel. Some embodiments of delivery systems, engagement mechanisms, implants, implant frames, and implant component configurations, expected delivered and expanded dimensions, and a description of target anatomy of some embodiments are provided herein.

The present disclosure provides various embodiments in which an implant can be delivered to a target area within a body lumen that has a very low diameter and therefore is difficult to reach using previous occlusion or delivery methods. Advantageously, some embodiments use a minimal number of components to effectuate occlusion of the body lumen, thus enabling the implant to be delivered using a low profile delivery catheter.

Accordingly, some embodiments provided herein relate to implantation in small blood vessels, such as from about 1 mm to about 20 mm, from about 2 mm to about 10 mm, or from about 3 mm to about 6 mm. The target delivery profile can be from about 1 Fr to about 20 Fr, and in some embodiments, from about 3 Fr to about 10 Fr. The target delivery profile can be about 8 Fr, about 7 Fr, about 6 Fr, about 5 Fr, about 4 Fr, about 3 Fr, or smaller.

Additionally, expansion of the implant can provide sufficient radial force against the inside wall of a vein. Some embodiments can comprise features or means configured to minimize backflow of blood or minimize venous insufficiency. For example, treatment applications for embodiments of the device can include ilio-femoral venous obstruction and chronic iliac venous outflow obstruction as a result of venous disease.

Some embodiments of the implants provided herein can be manufactured via several methods including shape-setting of drawn wire, chemical etching of a NiTi (nitinol) sheet of material, laser cutting of a tubular member, such as a material sheet or tubing, and/or electrical discharge machining (EDM) of a tubular member, such as a material sheet or tubing. Additionally, other alloys may also be employed in some circumstances, such as tantalum titanium and tantalum platinum titanium.

The implants disclosed herein can comprise flexible and/or shape memory materials such that they may be distorted from an expanded shape to a smaller diameter or straight shape to allow for delivery to a target location by way of a minimally invasive catheter-based approach.

In accordance with some embodiments, the implant can comprise a frame and an implant cover, cover component, or cover material. The frame can be covered with a non-permeable material, sealed at one or both ends to occlude blood flow. The cover component can comprise ePTFE tubing, film, and/or suture for attachment purposes. Additionally, the cover component may be fibrous, mesh-like, or impermeable in density.

The implant frame and/or cover component can comprise a collagen coating or collagen treatment to improve anchoring of the implant in the target vessel. The collagen can be configured to promote cell adhesion to implant materials, thereby facilitating improved support for the implant and vessel structure while acting as an anti-migration feature for the implant.

The implant frame can comprise a straight or constant diameter, a tapering diameter, or sections of variable diameter extending over its length, which can facilitate anchoring within a vessel and optimal deployment function.

Some embodiments of the systems and devices disclosed herein address the unmet need for a device that can provide a fast, precise and reliable way to close a bodily lumen. In some embodiments as used herein, occlusion may refer to partial or complete occlusion that can be temporary or permanent.

Frame configurations, expected delivered and expanded dimensions, and a description of target anatomy of some embodiments are provided. Some embodiments are provided by which the assembly, catheter, and/or implant can be advanced over a guidewire, thus allowing treatment of tortuous, distal, or smaller vessels in the vasculature. Aspects of implants, catheters, and delivery devices that can be utilized in combination with the implants, systems, methods, and features disclosed herein are disclosed in: U.S. patent application Ser. No. 12/826,593, filed on Jun. 29, 2010 (122270-5002); U.S. patent application Ser. No. 13/367,338, filed on Feb. 6, 2012 (122270-5006); U.S. patent application Ser. No. 12/906,993, filed on Oct. 18, 2010 (122270-5004); U.S. patent application Ser. No. 13/828,974, filed on Mar. 14, 2013 (122270-5014); U.S. Patent App. No. 61/835,406, filed on Jun. 14, 2013 (122270-5016); U.S. Provisional Application No. 61/835,461, filed on Jun. 14, 2013 (122270-5017); U.S. Patent Application No. 61/836,061, filed on Jun. 17, 2013 (122270-5020); U.S. patent application Ser. No. 14/044,794, filed on Oct. 2, 2013 (122270-5021); U.S. Provisional Application No. 61/900,321, filed on Nov. 5, 2013 (122270-5022); U.S. Patent App. No. 61/904,376, filed on Nov. 14, 2013 (122270-5023); U.S. Provisional Application No. 61/904,379, filed on Nov. 14, 2013 (122270-5025); U.S. patent application Ser. No. 14/101,171, filed on Dec. 9, 2013 (122270-5028); U.S. Provisional Application No. 61/939,659, filed on Feb. 13, 2014 (122270-5031); U.S. Patent App. No. 61/987,446, filed on May 1, 2014 (122270-5032); U.S. patent application Ser. No. 14/304,868, filed on Jun. 13, 2014 (122270-5035); U.S. patent application Ser. No. 14/628,096, filed on Feb. 20, 2015 (122270-5042); U.S. patent application Ser. No. 14/622,729, filed on Feb. 13, 2015 (122270-5041); U.S. patent application Ser. No. 14/697,547, filed on Apr. 27, 2015 (122270-5045); U.S. patent Ser. No. 14/973,414, filed Dec. 17, 2015 (122270-5052); and U.S. patent application Ser. No. 15/476,873, filed on Mar. 31, 2017 (122270-5064), the entirety of each of which is incorporated herein by reference.

The implants disclosed herein may utilize a frame or scaffold structure constructed using a single wire, enabling the frame to be fabricated in a simplified and cost effective manner. The single wire may be shaped to overlap over itself to form a dual wire loop configuration. The frame structure may also include a backbone support structure that may be formed as a longitudinal U shape or other shape variants. The backbone support provides unexpectedly high torque resistance for implantation stability and reduced migration risk while maintaining a minimum frame profile for facilitated implant insertion into small diameter body lumens.

Some embodiments of the implant can be used for purposes of tumor devascularization, calibrated flow and pressure reduction, reducing traumatic bleeding or hemorrhage, high-flow vascular malformations, vascular or airway volume reduction procedures, treatment of a target lesion, treatment and embolization of incompetent venous systems in low extremities (i.e., legs and lower abdominal area), treatment varicose veins in the leg (i.e., great saphenous vein and spider veins in deeper system), attending to other indications such as arteriovenous malformation (AVM), pelvic varices, and other such issues.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 6A-6F illustrate aspects of an occlusive implant scaffold, with a backbone support, on a catheter distal section of an implant carrier assembly, according to some embodiments.

DETAILED DESCRIPTION

Figure 1:
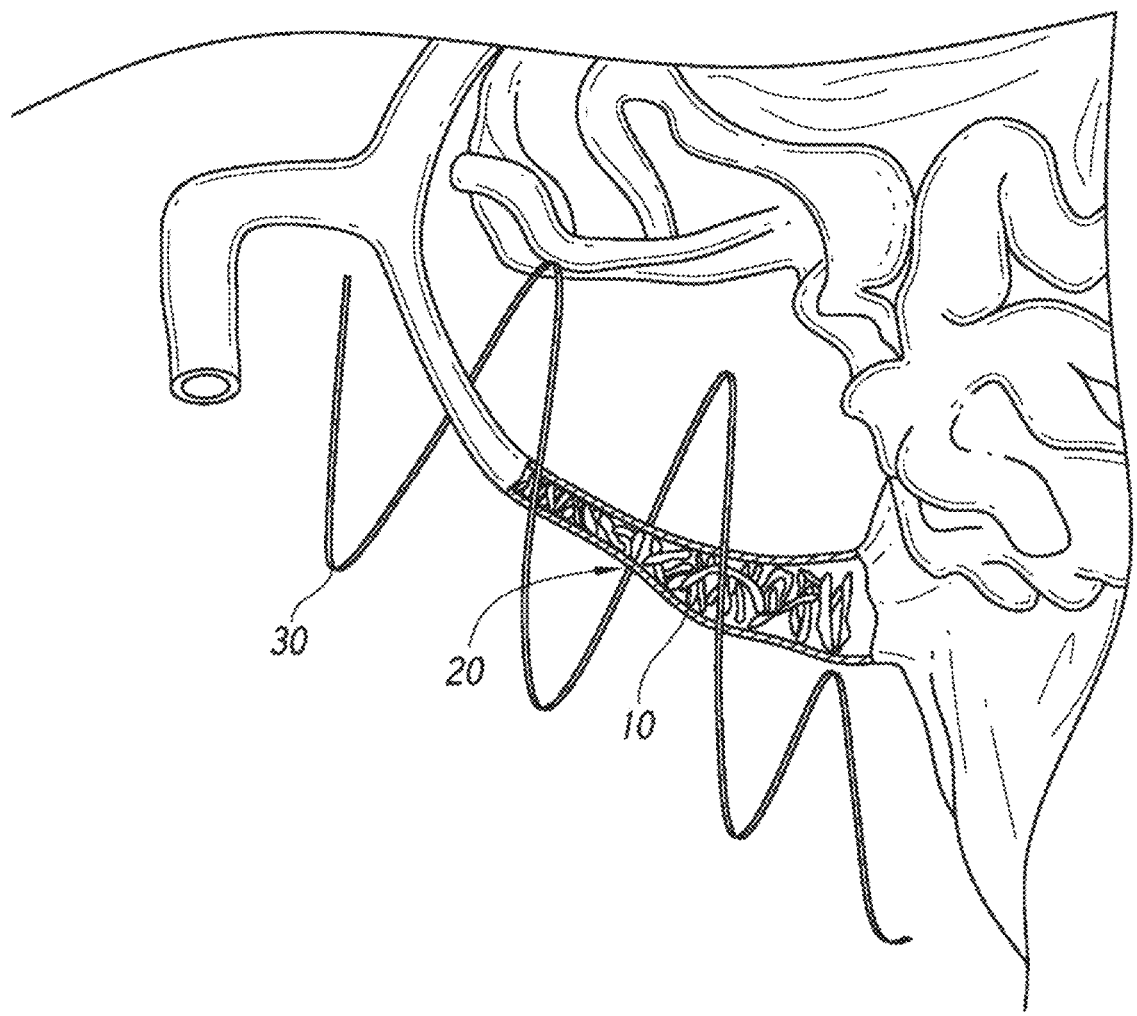
FIG. 1 illustrates a schematic view of a body lumen having an occlusive coil disposed therein.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

The present disclosure provides various embodiments of implant delivery systems and expandable occlusive implants that have a low-profile delivery configuration through a catheter, as well as methods of using the systems and implants. The implant can at least partially occlude or block flow in a body lumen, such as a blood vessel. Some embodiments can be configured to provide complete and immediate occlusion of target lumen using a low-profile implant having a frame and an occlusive component coupled to the frame. The implant can comprise a frame and a nonstructural occlusive component coupled to the frame that can both be positioned in a substantially linear configuration to minimize the cross-sectional profile of the implant in the delivery configuration. Thus, the implant can provide rapid and/or complete occlusion while enabling the implant, catheter, or system to have a low delivery profile, allowing the implant to be implanted into body lumens having a diameter of between about 1 mm and about 10 mm or between about 1 mm and about 20 mm.

For example, the catheter can define an outer diameter of less than 2 Fr (less than 0.667 mm), about 2 Fr (about 0.667 mm), about 3 Fr (about 1 mm), about 4 Fr (about 1.333 mm), about 5 Fr (about 1.667 mm), about 6 Fr (about 2 mm), about 7 Fr (about 2.333 mm), about 8 Fr (about 2.667 mm), about 9 Fr (about 3 mm), about 10 Fr (about 3.333 mm), about 11 Fr (about 3.667 mm), or about 12 Fr (about 4 mm), about 13 Fr (about 4.333 mm), about 14 Fr (about 5.667 mm), about 15 Fr (about 6 mm), or any dimension therebetween. These dimensions are provided for illustrative purposes only, and the size of the catheter disclosed herein can vary from these sizes.

According to some embodiments, a reduced diameter or reduced cross-sectional profile of the occlusive implant can be achieved by using a frame structure that can be collapsed or elongated into a substantially linear configuration. Further, the frame structure can have a nominal profile that is less than about five or ten times the cross-sectional profile of the filament(s) or wire forming the frame structure. For example, in some embodiments, the frame structure can be formed using at least one elongate wire that is drawn into a substantially linear configuration and moved through a catheter lumen toward the target site. Some embodiments can comprise two or more elongate wires that can be drawn into substantially elongate linear configurations. Accordingly, various embodiments can be provided in which the elongate wires are drawn into a minimum profile configuration that allows the stent to assume a collapsed configuration having a cross-sectional profile that allows the stent to be loaded and delivered using a very small gauge catheter.

Further, the frame structure may be constructed using a single wire, enabling the frame or scaffold to be fabricated in a simplified and cost effective manner. In some embodiments, the frame structure may include a backbone support structure that may be formed as a longitudinal U shape or other shape variant. Advantageously, the backbone support can provide unexpectedly high torque resistance for implantation stability and reduced migration risk while maintaining a minimum frame profile for facilitated insertion into small diameter body lumens. Optionally, the frame structure may be formed from a single wire that is deformed or shaped to overlap over itself to form a dual wire loop configuration, as described in U.S. patent application Ser. No. 14/304,868 (122270-5035).

Some embodiments of the implant frame can be comprise one or more features, such a variable pitch, an alternating pitch, a consistent pitch, a dual wire loop configuration, a single occlusive member, multiple occlusive members, occlusive members having different structures or material types, occlusive member coatings, and/or other features disclosed herein. Further, some embodiments can be used with valves, covers, fibrous membranes, and the like, such as disclosed in Applicant's copending U.S. patent application Ser. No. 14/304,868, filed on Jun. 13, 2014 (122270-5035), the entirety of which is incorporated herein by reference. Further, in accordance with some embodiments, the implants and delivery systems can be used in combination with image-guided placement techniques, such as fluoroscopy and the like. Additional details regarding these and other features are provided further below.

Occlusive Implants

FIG. 1 illustrates a schematic view of a body lumen 20 having an occlusive coil 10 disposed therein. Many conditions, including pelvic venous incompetence, create the need to close blood vessels that have lost their integrity. FIG. 1 illustrates the use of microcoil embolization to permanently insert occlusive implant 10 into body lumen 20, wherein occlusive implant 10 includes a large number of metallic coils. However, this approach suffers from several drawbacks, including significant exposure of x-ray radiation 30 to the patient, permanent insertion that does not permit easy removal, and limited application to smaller diameter body lumens due to the large volume of implant material within occlusive implant 10.

Figure 2A:
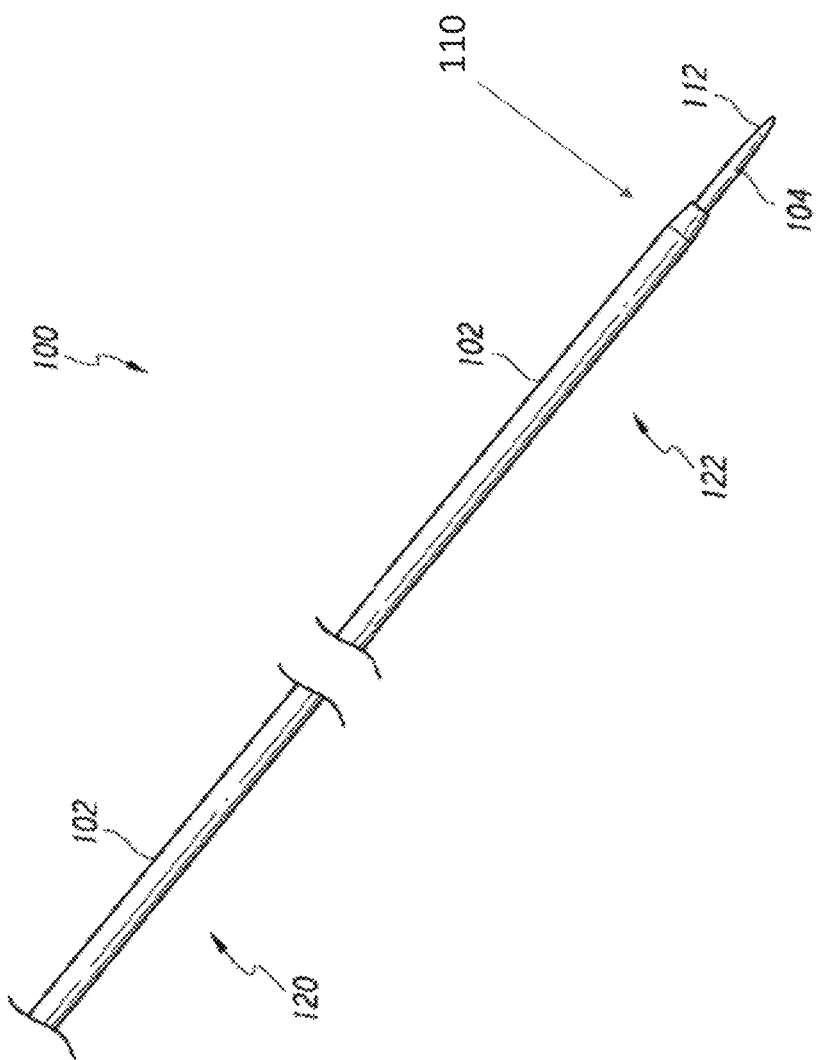
FIG. 2A illustrates a top view of a guide sheath assembly, according to some embodiments.

Accordingly, some embodiments comprise a guide sheath assembly that can be used to access a treatment site. The guide sheath assembly can be advanced to the treatment site, to deploy one or more devices, is disclosed herein. For example, FIG. 2A illustrates a guide sheath assembly 100 that comprises a guide sheath 102 and a removable core 104. In some embodiments, the guide sheath assembly 100 can be advanced over a wire to the treatment site. However, the guide sheath assembly 100 can also be configured to be advanced independently or without a wire.

The guide sheath assembly 100 can be configured such that the removable core 104 can fit inside a lumen of the guide sheath 102 and extend out of a distal end 110 of the sheath 102. The removable core 104 can comprise a distal tip 112 that can be configured to be atraumatic. For example, the distal tip 112 can be rounded (for example, in embodiments that are advanced over a wire) and/or comprise an atraumatic tip coil (for example, in embodiments that are advanced independently or without a wire).

The guide sheath 102 can comprise a braided shaft with a stiff proximal section 120 and a more flexible distal section 122 to enable tracking through tortuous peripheral vasculature. The guide sheath distal end 110 can be tapered and include a radiopaque marker that is visible under fluoroscopy. In some embodiments, the guide sheath 102 can include a radiopaque marker at a proximal end.

In accordance with some embodiments, the total length of the guide sheath 102 can have a total length from about 40 cm to about 150 cm, from about 60 cm to about 120 cm, or from about 70 cm to about 90 cm. For example, in some embodiments, the total length of the guide sheath 102 can have a total length of about 80 cm. Further, some embodiments, the guide sheath 102 can have a working length from about 65 cm to about 110 cm, from about 75 cm to about 100 cm, or in some embodiments, about 89 cm.

Additionally, in some embodiments, the removable core can 104 have a lumen (not shown) through which a guidewire can extend and a tapered end 112 for ease of advancement into and through the blood vessel. The total length of the removable core 104 can be from about 50 cm to about 180 cm, from about 70 cm to about 150 cm, or in some embodiments, about 110 cm, with a working length of from about 85 cm to about 130 cm, from about 95 cm to about 120 cm, or in some embodiments, about 108 cm.

In order to place the guide sheath assembly 100 in a vessel of the body, a guide wire (having a diameter of 0.035") can be placed into the vessel, and the guide sheath 102 and removable core 104 can be advanced over the guide wire. The guide wire and removable core 104 can then be removed from the guide sheath 102 once the guide sheath 102 is in position for delivery of the implant.

After the guide sheath 102 is placed, an implant carrier assembly can be inserted into the guide sheath 102 and advanced to the treatment site.

Figure 2B:
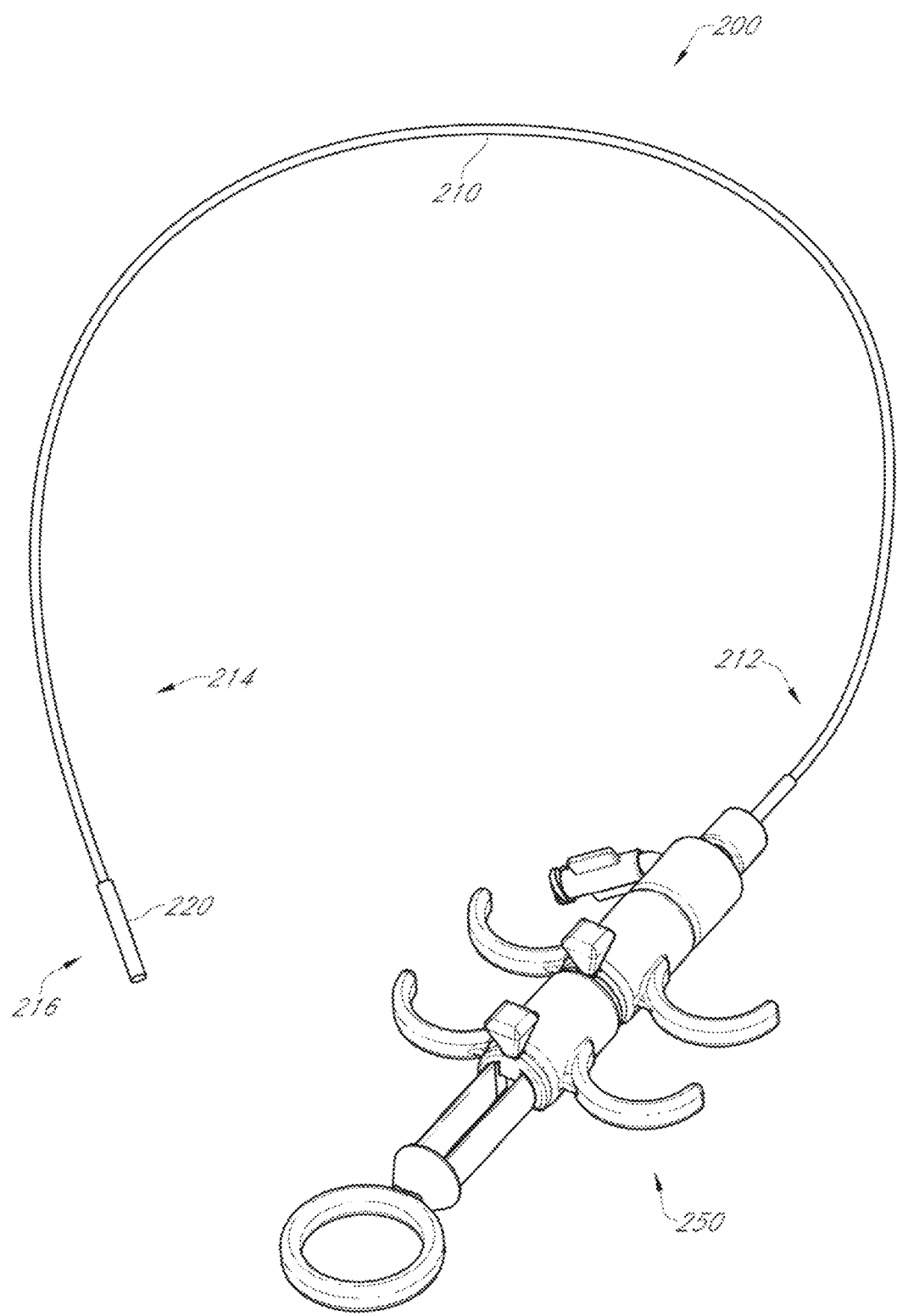
FIG. 2B illustrates a perspective view of an implant carrier assembly, according to some embodiments.

FIG. 2B illustrates an embodiment of an implant carrier assembly 200 can comprise a catheter 210 having a lumen that extends between a proximal portion 212 and a distal portion 214 of the catheter. The catheter 210 can also comprise a distal engagement section 216 configured to engage and/or restrain an implant position thereabout. The catheter 210 can define a length from about 50 cm to about 200 cm, from about 70 cm to about 160 cm, or in some embodiments, about 120 cm, with a working length of from about 85 cm to about 140 cm, from about 95 cm to about 130 cm. In accordance with some embodiments, the total length of the implant carrier assembly (with handle) can be about 117 cm, with a working length of 97 cm.

The assembly 200 can also comprise an implant 220 loaded on the engagement section 216. Further, the assembly 200 can also comprise a deployment handle assembly 250 attached to the catheter proximal portion 212.

As noted above, the catheter 210 can be configured to within the guide sheath 102. The proximal portion 212 of the catheter 210 can have be configured to be relatively stiff in order to enhance the pushability of the catheter 210 through the guide sheath 102. Further, the distal portion 214 can be relatively flexible in order to improve the maneuverability and trackability of the catheter 210 as it is advanced through the guide sheath 102.

FIGS. 3A-3G illustrate several views of an embodiment of an expandable frame or scaffold 302 for the occlusive implant. FIGS. 3A-3G illustrate the scaffold 302 in a neutral or default state, whereto the scaffold 302 has been permitted to expand without being restricted to a catheter or other delivery device. Further, it should be understood that FIGS. 3A-3G only illustrate one example of scaffold 302 and other implementations may use, for example, different loop quantities, different backbone support shapes, or other variations.

Figure 3A:
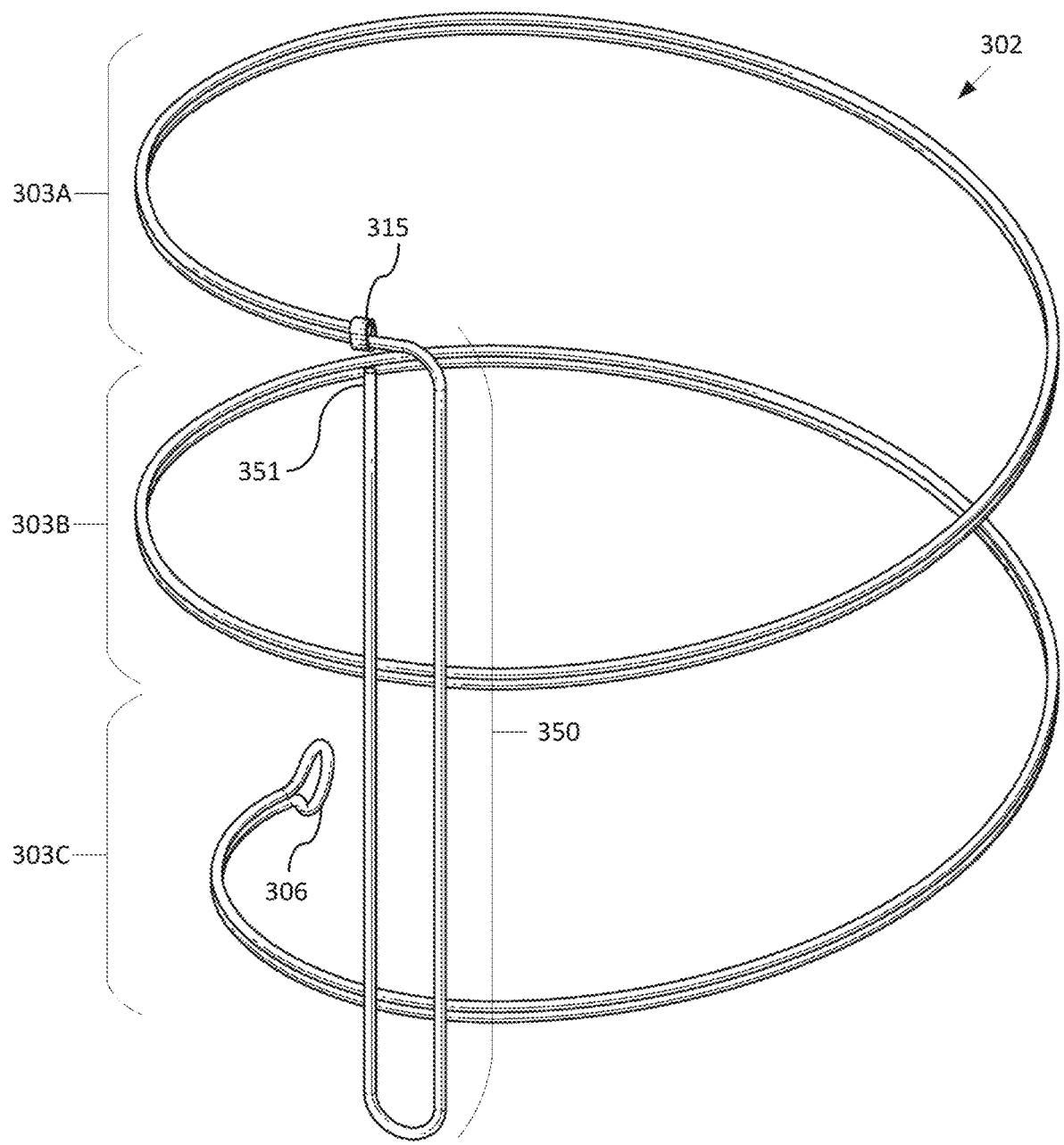
FIG. 3A illustrates a perspective view of an occlusive implant scaffold with a backbone support, according to some embodiments.

FIG. 3A illustrates a perspective view of the frame or scaffold 302 with backbone support 350, according to some embodiments. The scaffold 302 may comprise a plurality of loops, or loops 303A-303C. A first end portion of the scaffold 302 may connect to handle 306, and a second end portion of the scaffold 302 may connect to clip 315. As shown in FIG. 3A, the handle 306 may comprise a ring shape, but other shapes may be utilized. The scaffold 302 may include one or more partial or complete loops, wherein the example shown in FIG. 3A may include two complete loops 303A and 303B and one partial loop 303C. Thus, 2-3 loops, 2-4 loops, 3-5 loops, 3-6 loops, 4-7 loops, or any range of loops may be provided in scaffold 302.

As illustrated further below in FIGS. 3F and 3G, the loops 303A, 303B, and 303C may have substantially similar curvatures such that the loops 303A-303C appear to overlap in a top plan view. However, loop 303C that is connected to handle 306 may have a smaller curvature than the other loops 303A and 303B. This reduced curvature may facilitate handling and retrieval of handle 306.

Loops 303A-303C may be formed in a dual wire loop configuration as shown. In some implementations, a substantial entirety of scaffold 302 may be formed with a single, continuous wire. For example, the wire may begin at clip 315, extend through loops 303A-303C into handle 306, whereat the wire reverses path back to clip 315 through loops 303A-303C to form the dual wire loop configuration. The wire may continue extending to form backbone support 350, providing a U shape before terminating at end portion 351. This may enable cost efficient manufacture of scaffold 302 while mechanically reinforcing the shape of scaffold 302. Clip 315 or another fastening mechanism may be provided to reinforce a coupling point between loops 303A-303C and backbone support 350.

As shown in FIG. 3A, the backbone support 350 may be provided in a substantially U shaped form, similar to a paper clip shape. The backbone support 350 may extend across at least the entire longitudinal length of scaffold 302. Further, the backbone support 350 may terminate at end portion 351, wherein end portion 351 is in substantially close proximity to the other end portion of backbone support 350 that is connected to loop 303A via clip 315 indicating the coupling point. The close proximity may help to provide greater mechanical support.

For example, in some implementations, the end portion 351 may be restricted to a position anchored by the coupling point indicated by clip 315. In some implementations, the restriction may correspond to a distance from clip 315 that does not exceed a percentage of the total longitudinal length of backbone support 350, such as no further than 1%, 2%, 3%, 5%, 10%, or some other percentage. In some implementations, the end portion 351 may not exceed a predefined distance from clip 315.

In other implant devices, zig-zag loop structures placed at various angles or other complex frame designs may be utilized to provide sufficient torque resistance against dislodging and migration of the implant. These other implant devices may be difficult and costly to manufacture. On the other hand, the U shaped form of backbone support 350 positioned on a single side of scaffold 302 provides an unexpectedly robust torque resistance for implantation stability and reduced migration risk. The scaffold 302 may be shaped using a single wire in a dual wire loop configuration for cost efficient manufacture with minimized material requirements while maintaining high structural and mechanical integrity. Further, since the backbone support 350 is positioned on one side of the outside perimeter of scaffold 302, scaffold 302 can still be readily collapsed into a low profile, reduced cross sectional area compressed form for positioning onto catheters or other delivery devices, thereby facilitating insertion into small diameter body lumens. Yet further, integrated handle 306 facilitates handling of scaffold 302, providing flexibility for repositioning and removal of the implant.

Figure 3B:
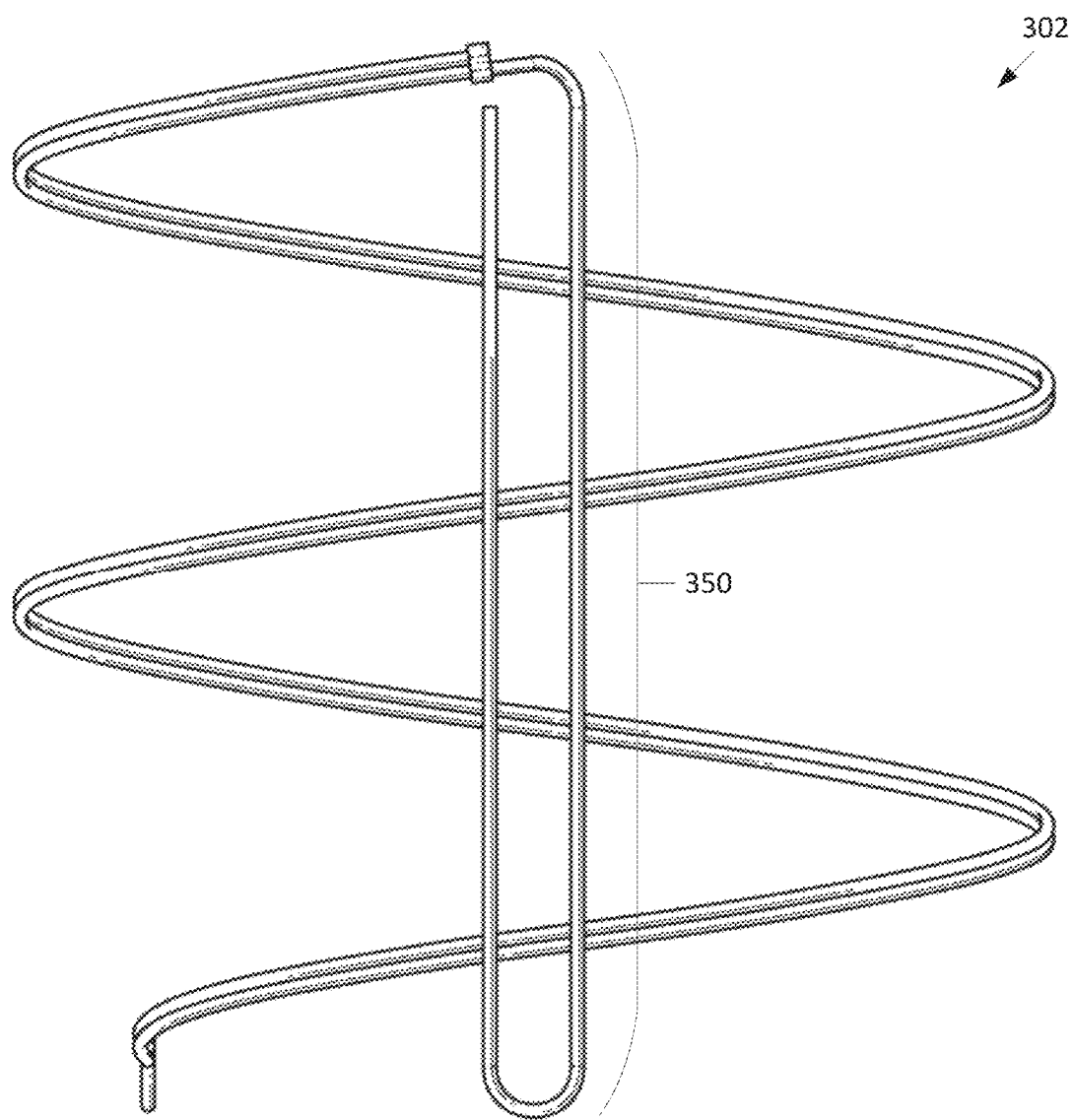
FIG. 3B illustrates a side view facing the backbone support of the occlusive implant scaffold of FIG. 3A.

FIG. 3B illustrates a side view facing backbone support 350 of scaffold 302 of FIG. 3A. The backbone support 350 may lie on an outer perimeter of scaffold 302 and be substantially flat. Further, it can be seen that backbone support 350 extends substantially across the entire longitudinal length of scaffold 302.

Figure 3C:
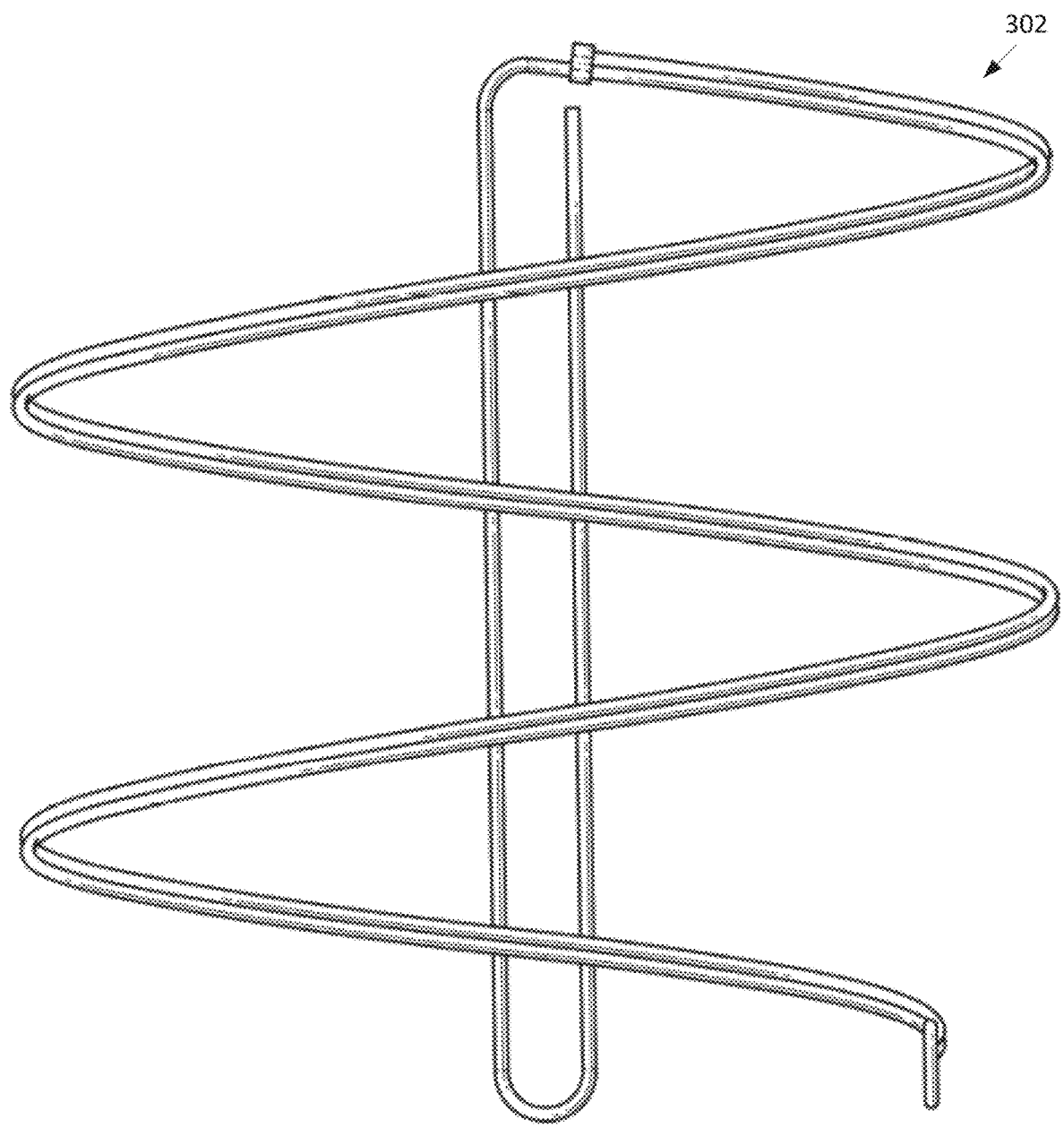
FIG. 3C illustrates a side view facing an opposite side of the backbone support of the occlusive implant scaffold of FIG. 3A, according to some embodiments.

FIG. 3C illustrates a side view facing an opposite side of backbone support 350 of scaffold 302 of FIG. 3A, according to some embodiments. As shown in FIG. 3C, the loops of scaffold 302 may not extend beyond backbone support 350.

Figure 3D:
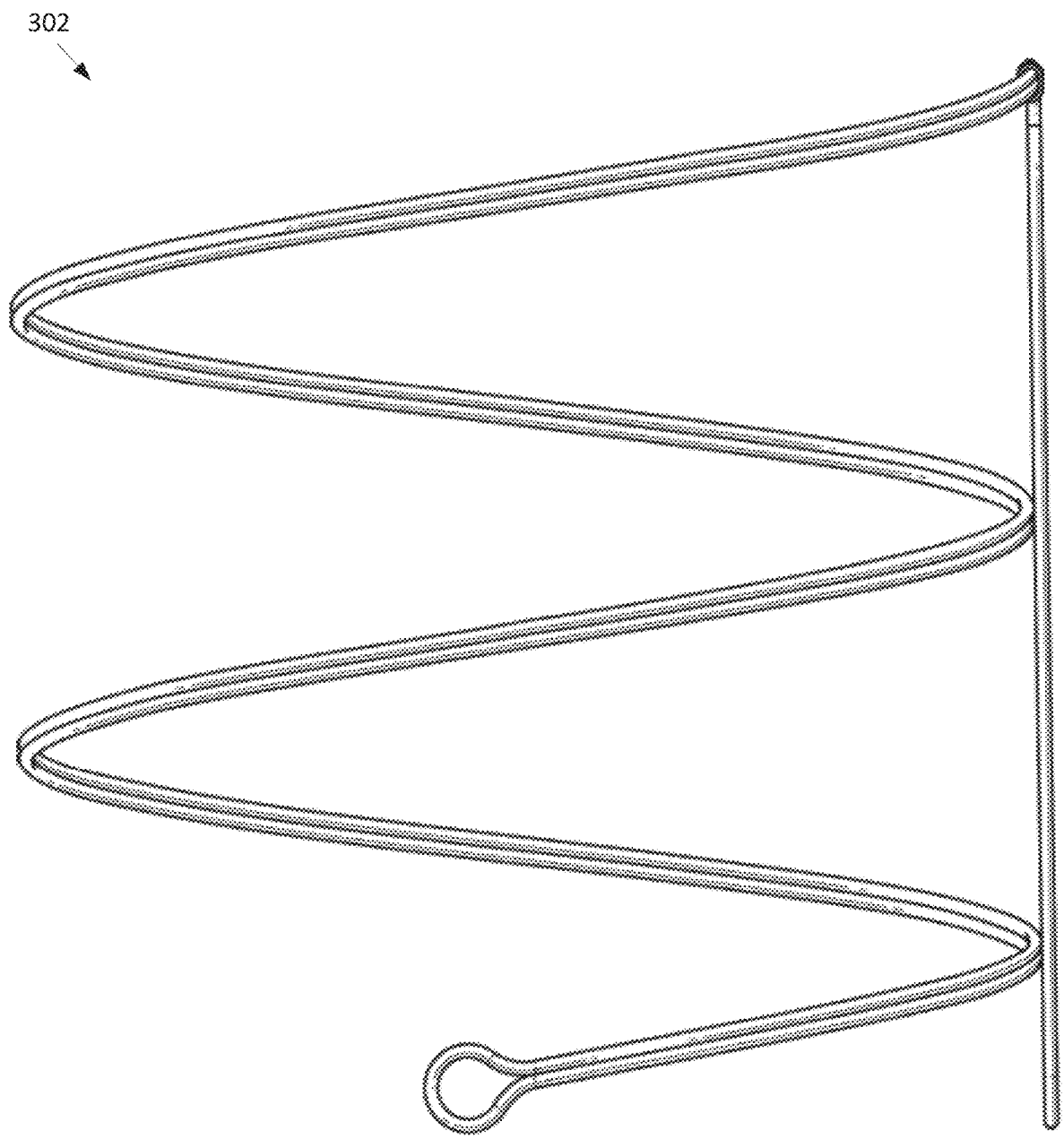
FIG. 3D illustrates a side view of the occlusive implant scaffold of FIG. 3A with the backbone support positioned on a right side, according to some embodiments.
Figure 3E:
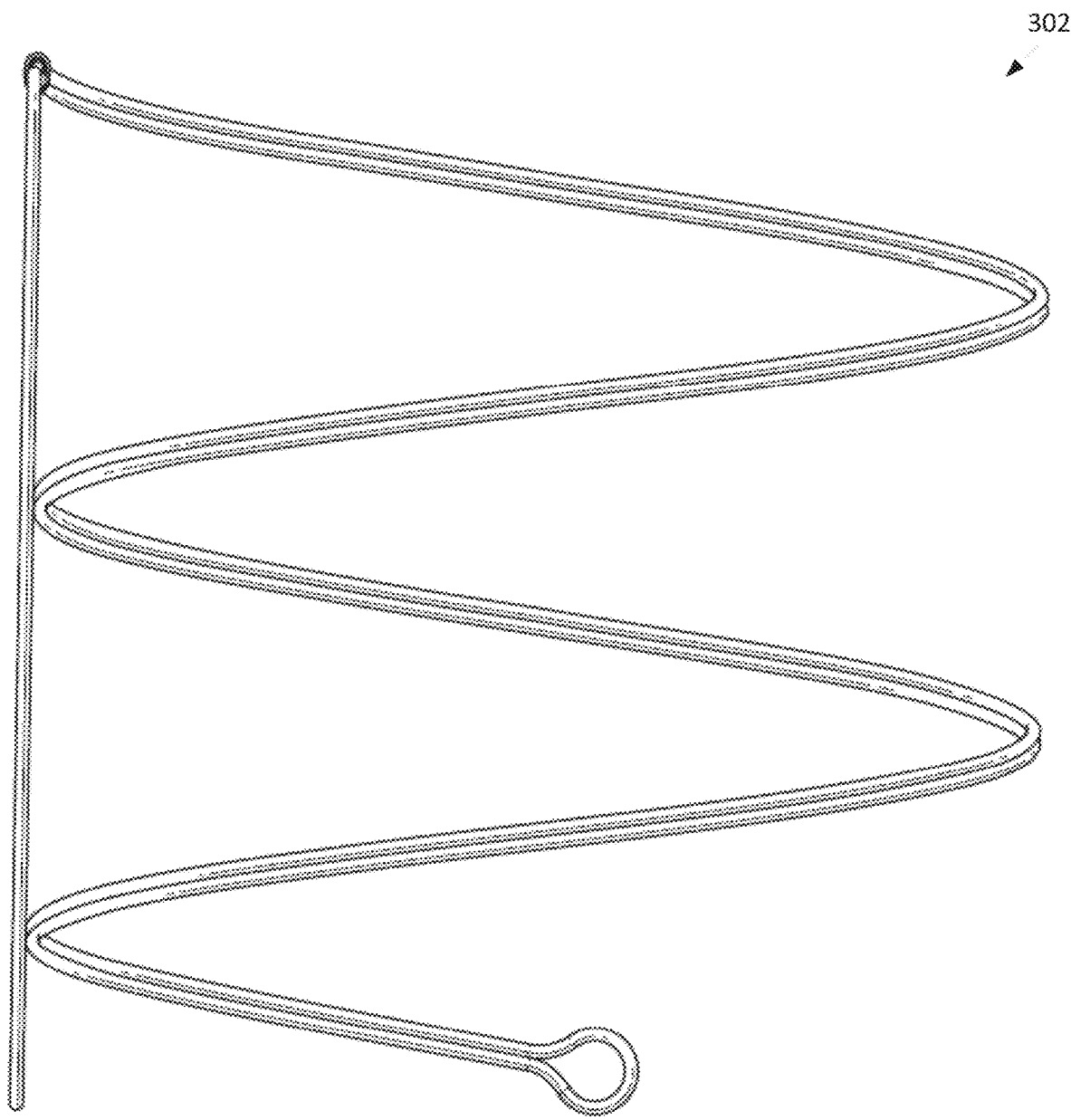
FIG. 3E illustrates a side view of the occlusive implant scaffold of FIG. 3A with the backbone support positioned on a left side, according to some embodiments.

FIG. 3D and FIG. 3E illustrate side views of scaffold 302 of FIG. 3A with backbone support 350 positioned on right and left sides, respectively, according to some embodiments. As shown in FIGS. 3D and 3E, the backbone support 350 may lie in a common plane (be coplanar) or be substantially flat when seen in side view.

Figure 3F:
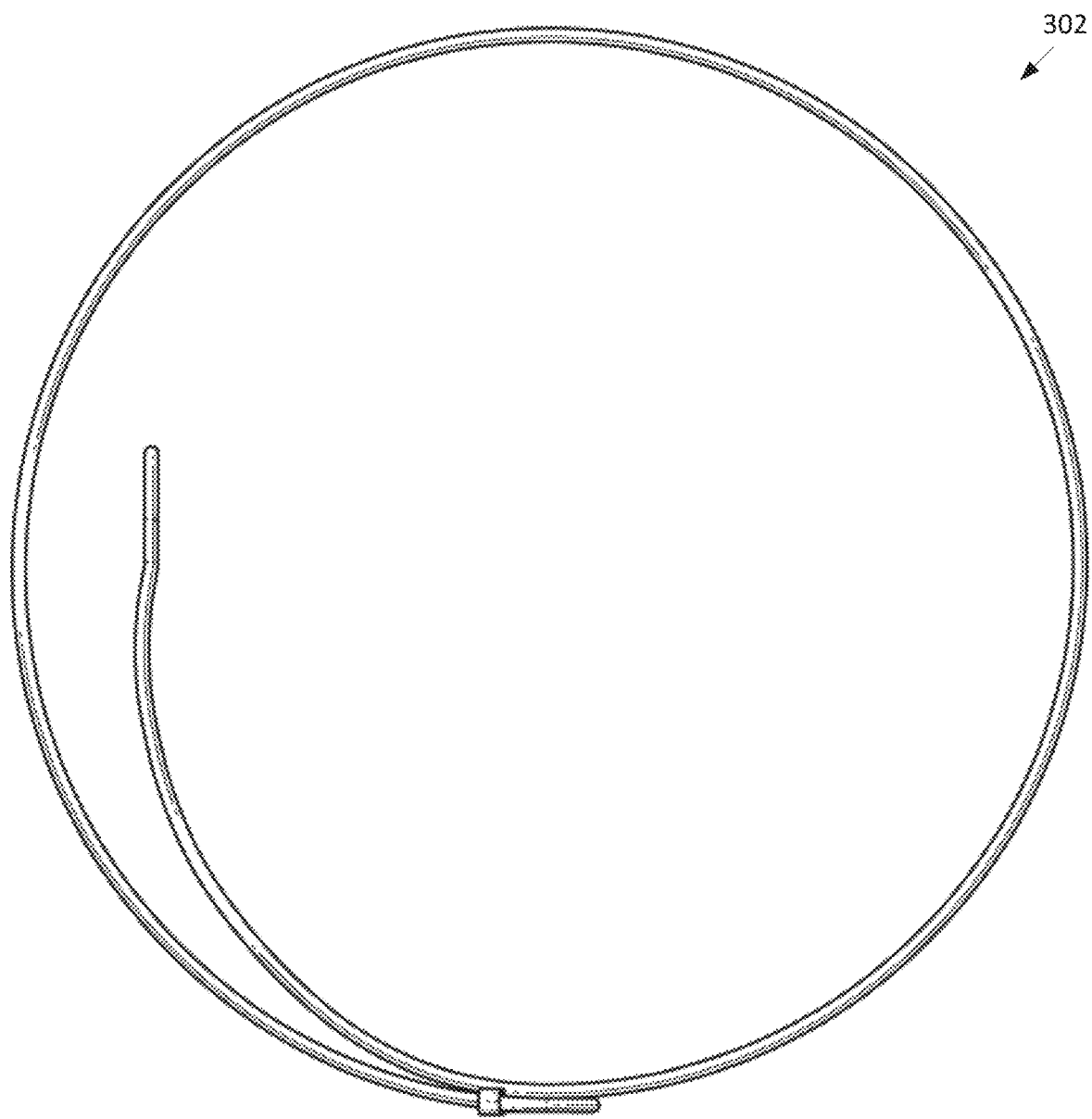
FIG. 3F and FIG. 3G illustrate top plan views of the occlusive implant scaffold of FIG. 3A, according to some embodiments.
Figure 3G:
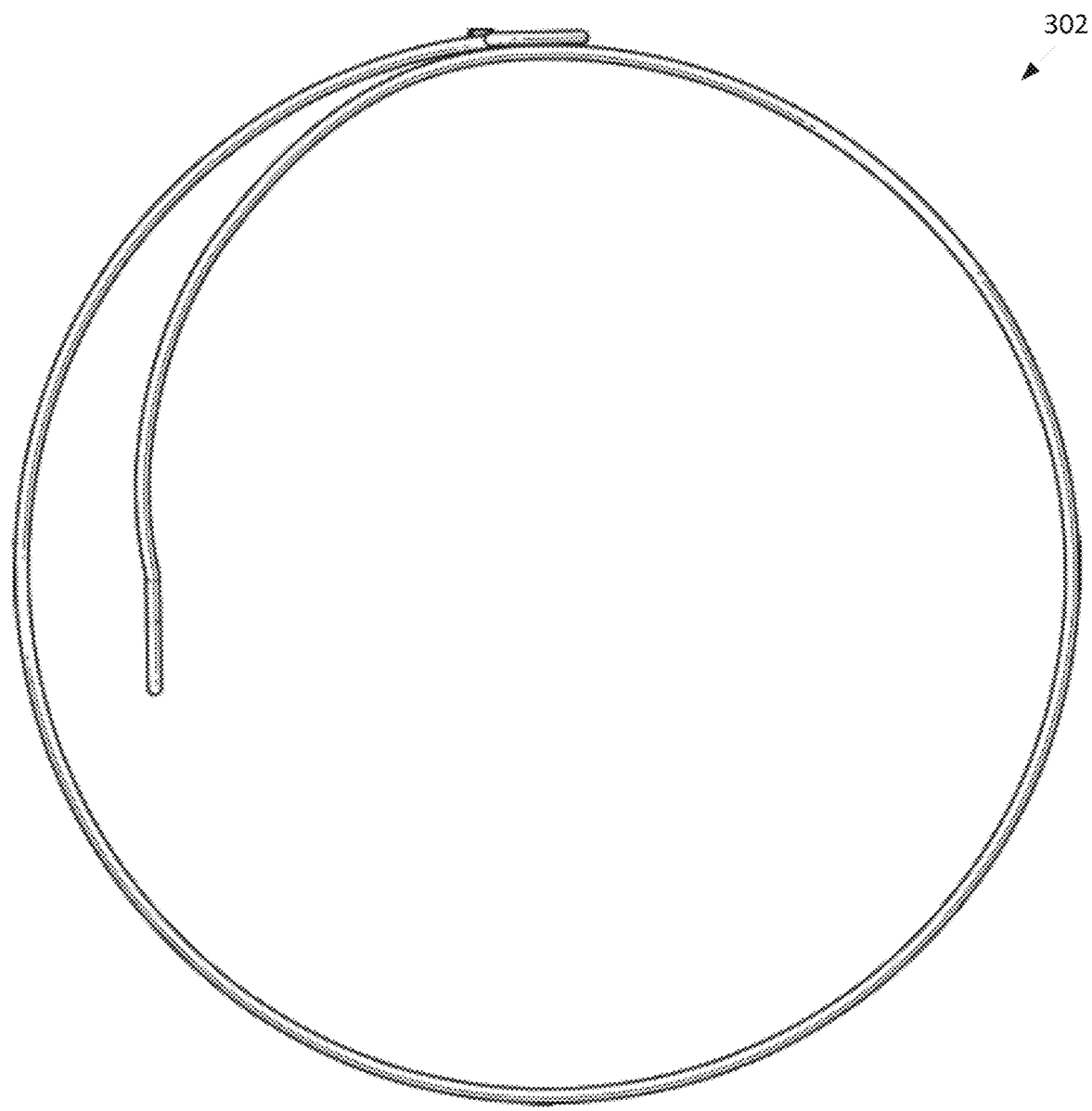

FIG. 3F and FIG. 3G illustrate top plan views of scaffold 302 of FIG. 3A, according to some embodiments. As shown in FIG. 3F and FIG. 3G, the loops may have substantially similar curvatures so that the loops appear to overlap when viewed from a top plan view. However, the loop that is connected to backbone support 350 may have a smaller radius of curvature compared to the other loops.

Figure 4:
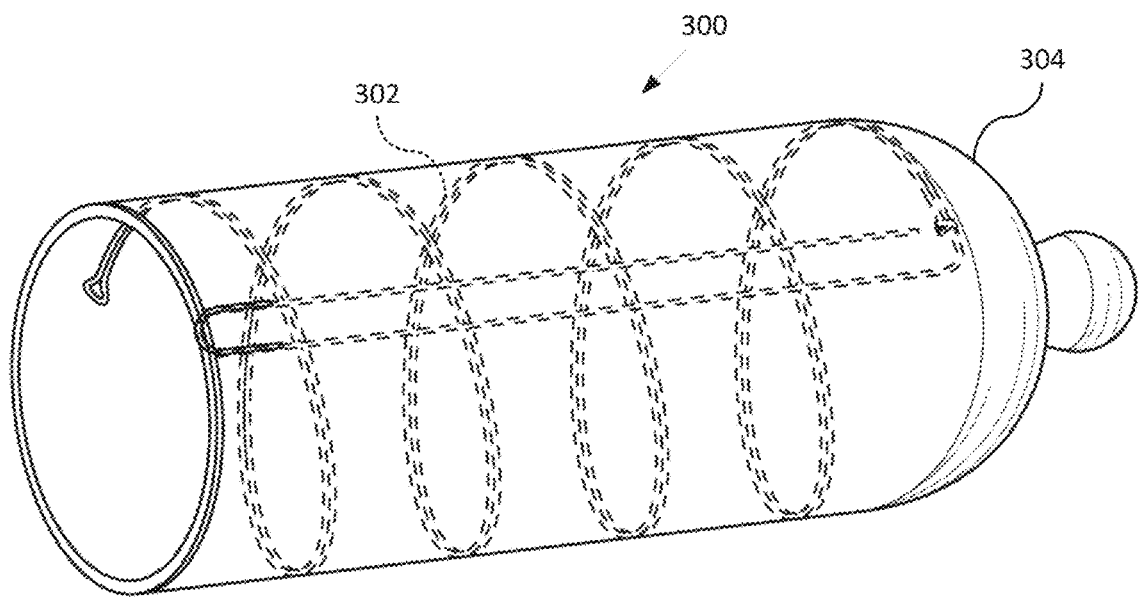
FIG. 4 illustrates a perspective view of an occlusive implant with a backbone support, according to some embodiments.
Figure 5:
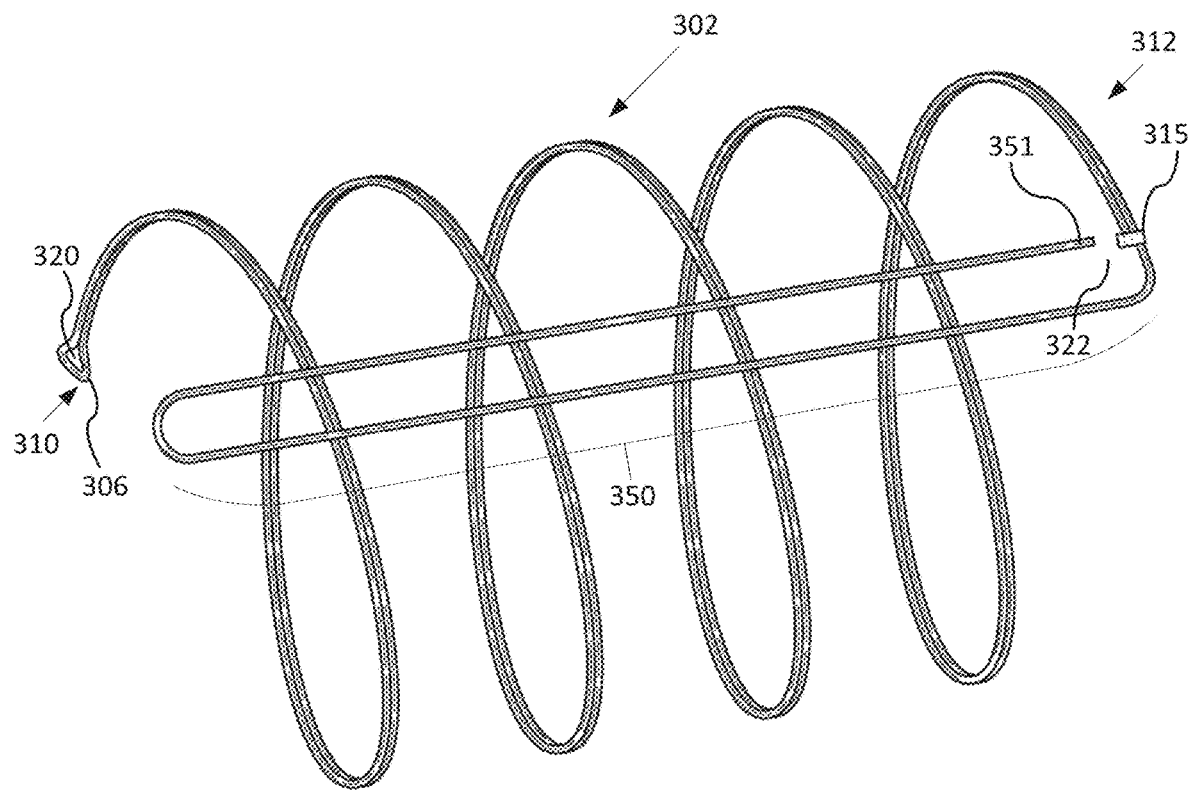
FIG. 5 illustrates a perspective view of a scaffold of an occlusive implant with a backbone support, according to some embodiments.

Referring now to FIGS. 4 and 5, features of an embodiment of an implant 300 with backbone support 350 are illustrated. The implant 300 can comprise a scaffold 302 and a membrane 304 supported by the scaffold 302. In some implementations, membrane 304 may extend across at least the entire longitudinal length of scaffold 302. As shown in FIG. 4, scaffold 302 may include approximately four (4) full loops and one partial loop. However, as discussed above, various loop quantity ranges may be provided. The scaffold 302 can be formed from a variety of materials, which can be flexible or deformable. For example, the scaffold 302 can comprise nitinol. Additionally, the membrane 304 can comprise one or more of a variety of materials that can be impermeable or have low permeability. In some embodiments, the membrane 304 can be configured to occlude blood flow. For example, the membrane 304 can comprise polytetrafluoroethylene (PTFE), and similar materials, such as expanded polytetrafluoroethylene (ePTFE).

When implanted into a vessel, the implant 300 with backbone support 350 can be configured to provide sufficient radial strength against a vessel wall under normal blood pressure in order to minimize post-deployment migration.

The implant 300 can be configured with an expanded diameter depending on the target vessel size. For example, the implant 300 can have an expanded diameter of about 6 mm for vessels from about 3.0 mm to about 4.8 mm in diameter. Further, the implant can have an expanded diameter of about 9 mm for vessels from about 4.5 mm to about 7.8 mm in diameter. Additionally, such embodiments can be compatible with, for example, a 6 fr guiding catheter.

Referring now to FIG. 5, in some embodiments, the implant scaffold 302 can be formed as a helical body. For example, the scaffold 302 can define a proximal section 310 in proximity to handle 306 and a distal section 312 in proximity to clip 315. Generally, the body of the scaffold 302 can extend along a curvilinear, helical path. However, in accordance with some embodiments, one or both of the proximal or distal sections 310, 312 can bend radially inwardly from the helical path. In some embodiments, one or both of the proximal or distal sections 310, 312 can be configured to extend across the lumen of the scaffold 302, and/or across the lumen of the catheter 210, as discussed further below.

For example, the proximal section 310 can be configured to include an elbow that causes a portion of the proximal section 310 to diverge from the generally helical path of the scaffold 302. The elbow may include handle 306 and can comprise a change to a smaller radius of curvature compared to the radius of curvature of the helical path. This may be more easily observed in the top plan views of FIGS. 3F and 3G. Further, in some embodiments, the elbow can define a generally right angle orientation for the proximal section 310.

Additionally, in some embodiments, the distal section 312 can also comprise an elbow. The elbow can be configured similarly to the elbow of the proximal section 310 and allow a divergence in the path of the scaffold 302 at the distal section 312 thereof.

Further, in some embodiments, one or both of the proximal or distal sections 310, 312 can comprise a generally planar portion. For example, the proximal section 310 can comprise a planar portion, or handle 306. The handle 306 can comprise a portion of the proximal section 310 that diverges from the helical path and extends generally within a plane. Thus, the handle 306 can be referred to as a flat or flattened portion that can extend in a generally linear or curvilinear direction within a plane. In some embodiments, the distal section 312 can also comprise a planar portion, which is illustrated in FIG. 5 as backbone support 350.

The planar portions, whether either or both of them are included in an embodiment, can extend or bend radially inwardly from the helical path of the scaffold 302. Similarly, backbone support 350 can be configured to extend across the lumen of the scaffold 302, and/or across the lumen of the catheter 210, as discussed further below.

The scaffold 302 can comprise one or more reduced cross-sectional segments 320, 322. The segments 320, 322 can be disposed at the proximal section 310 and/or the distal section 312 of the scaffold 302. For example, FIG. 5 illustrates that the proximal section 310 comprises the reduced cross-sectional segment 320 and the proximal section 312 comprises a reduced cross-sectional segment 322.

In the illustrated embodiment, the reduced cross-sectional segments 320, 322 can comprise handles such as rings, U shapes, or other forms within the body of the scaffold 302. For example, the scaffold 302 can comprise a generally dual cylindrical cross section and extend helically about a central axis or lumen, as illustrated in FIG. 5.

The reduced cross-sectional segments 320, 322 can optionally comprise indentations, protrusions, slots, openings, and/or apertures extending through the scaffold 302. As discussed further below, the segments 320, 322 can be configured to interact with respective structures of the engagement section 216 of the catheter 210.

Figure 6A:
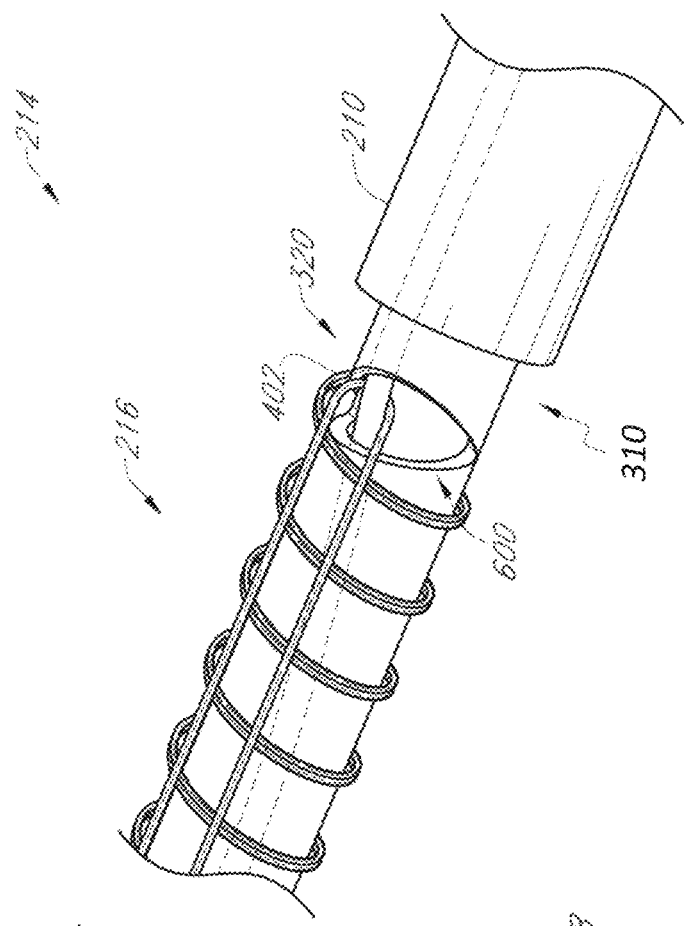

For example, FIGS. 6A-6D illustrate some embodiments of implant carrier assemblies. FIG. 6A illustrates an enlarged view of a distal engagement section or seat 216 located at a distal portion 214 of the catheter 210. The catheter 210 can comprise a lumen 400 extending through the catheter 210 and a catheter wall 402 formed between the catheter lumen 400 and an exterior surface 404 of the catheter 210.

As shown in FIG. 6A, the distal engagement section 216 can be configured to receive and facilitate engagement with at least a portion of an implant (illustrated only as scaffold 302, but which can include a membrane, as discussed above) to maintain the implant engaged with the distal end 214 of the catheter 210.

In accordance with some embodiments, the implant carrier assembly 200 can also be configured to comprise at least one elongate member 420 that extends at least partially through the catheter lumen 400. The elongate member 420 can engage at least a portion of, and in some embodiments, one or both the proximal and distal sections 310, 312, of the scaffold 302. The elongate member 420 can comprise a wire. However, in some embodiments, the elongate member 420 can comprise a plug or other structure that can interact with one or both of the proximal or distal sections 310, 312 of the implant 300.

In some embodiments, the elongate member 420 can be actuatable or controllable using the handle assembly 250, as discussed further below.

For example, the engagement section 216 can be configured to facilitate engagement between the scaffold 302 and the elongate member 420 extending from the handle assembly. In some embodiments, the elongate member 420 can be selectively actuated or withdrawn in order to release engagement between the scaffold 302 in the elongate member 420. The movement of the elongate member 420 can be configured to be a proximal withdrawal of the elongate member 420. However, the elongate member 420 can also be configured such that disengagement occurs when the elongate member is distally advanced (such as when a proximally oriented hook or segment of the elongate member 420 engages with the scaffold 302). Indeed, the elongate member 420 can be moved a first distance (whether proximally or distally) in order to release or disengage with one of the proximal or distal sections 310, 312 of the scaffold 302. Further, the elongate member can be moved a second distance, greater than the first distance (whether proximally or distally) in order to release or disengage with the other one of the proximal or distal sections 310, 312 of the scaffold 302.

Further, in some embodiments, the engagement section 216 can facilitate engagement between the implant 300 and two or more elongate members 420 extending from the handle assembly 250. Although the elongate member 420 is illustrated as extending between the proximal and distal sections 310, 312 of the implant scaffold 302, the elongate member 420 can engage one of the proximal or distal sections 310, 312 while a second elongate member can be used to engage the other of the proximal or distal sections 310, 312.

For example, FIG. 6B illustrates an embodiment of an implant assembly in which a catheter 500 comprises an engagement section 502 and a lumen 504. The assembly can comprise an implant or scaffold 510 supported on the engagement section 502. Further, the assembly can comprise a first elongate member 520 and a second elongate member 522 configured to engage with the scaffold 510. As shown, a distal portion 530 of the elongate member 520 can engage a distal portion 540 of scaffold 510 and a proximal portion 532 of the elongate member 522 can engage with a proximal portion 542 of the scaffold 510.

Accordingly, in embodiments that comprise two elongate members, the elongate members can be actuated independently of each other in order to control the release of the respective proximal or distal sections 310, 312 of the scaffold 302 or implant 300.

Referring again to FIG. 6A, the catheter 210 can be configured to comprise at least one aperture. For example, the catheter 210 illustrated in FIG. 6A comprises a proximal aperture 600 and a distal aperture 602. The proximal and distal aperture 600, 602 are configured to extend through the wall 402 of the catheter 210. Further, the apertures 600, 602 are configured as slots or notches that extend transversely relative to a longitudinal axis of the catheter lumen 400. The apertures 600, 602 can extend radially at least partially into the lumen 400, and as illustrated, can extend about halfway across a diameter of the lumen 400. In some embodiments, the aperture 600, 602 can extend radially through from about ¼ to about ¾ of the diameter of the lumen 400, through from about ⅓ to about ⅔ of the diameter of the lumen 400, or in some embodiments, through about ½ of the diameter of the lumen 400.

For example, as illustrated in FIG. 6B, some embodiments can be configured such that at least one of the proximal or distal sections 310, 312 of the scaffold 302 extends within the respective proximal or distal aperture 600, 602 of the catheter 210.

Further, FIG. 6B also illustrates the scaffold 302 of the implant 300 in a mounted, collapsed, or wound position. In the mounted, collapsed, or wound position, the scaffold 302 can be wound around the catheter distal portion with about 10 to about 25 winds, from about 15 to about 20 winds, or in some embodiments about 16 or about 19 winds. Thus, before the scaffold 302 or stent 300 is released, the scaffold 302 is helically wound tightly around the catheter 210. The winding of the scaffold 302 about the catheter distal portion can put the scaffold 302 into a stressed state. As discussed further below, the scaffold 302 will tend to rebound or expand from the stressed, mounted, collapsed, or wound position.

Additionally, some embodiments can be configured such that an elongate member extends through the catheter lumen and between at least one of the proximal or distal sections of the scaffold and the wall of the catheter. For example, the elongate member can be disposed radially between the proximal or distal section of the scaffold and the wall of the catheter.

Figure 6C:
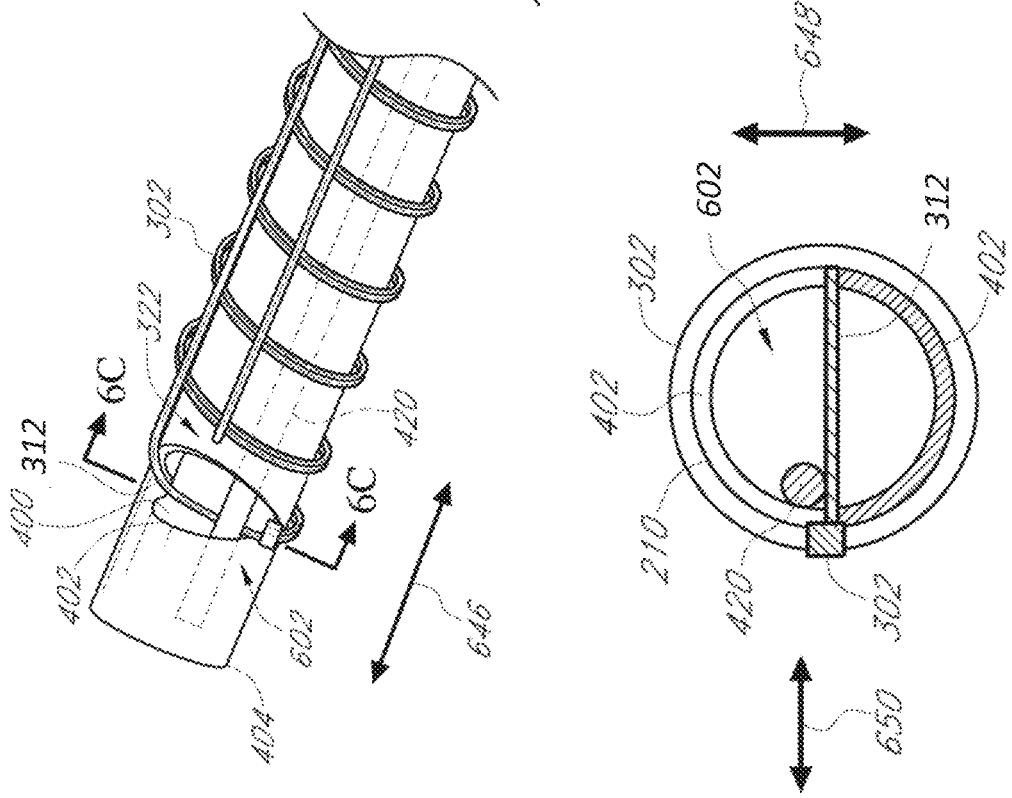

For example, FIG. 6C illustrates the configuration of the catheter 302 and the aperture 600 in relation to the elongate member 420 and the distal section 312 of the scaffold 302. As shown, the distal section 312 can sit within the aperture 602 and provide enough clearance between the distal section 312 and wall 402 or the inner surface of the wall 402 such that the elongate member 420 can be positioned intermediate the wall 402 and the distal section 310. As also shown, the distal section 312 can extend across the entire diameter of the lumen 400 and a transverse direction. However, the proximal and/or distal sections 310, 312 can also be configured to extend across the lumen 400 less than a diameter of the lumen 400 (whether in the transverse direction or in a radial direction).

Accordingly, the elongate member 420 can secure the distal section 312 within the aperture 600 to prevent movement of the proximal section in an axial direction 646 (shown in FIG. 6A) and/or a radial direction 648 (shown in FIG. 6C). In some embodiments, the scaffold 302 can be a resilient or self-expanding scaffold, such that the distal section 312 will tend to expand or move out of the aperture 600 without the presence of the elongate member 420. Thus, when the elongate member 420 is in place between the distal section 312 and the wall 402 of the catheter 210, the distal section 312 can be retained or engaged within the aperture 600.

The engagement illustrated in FIG. 6C between the distal section 312, the elongate member 420, and the aperture 600 can also be present at the proximal end of the scaffold 302, although it will not be discussed further herein. However, as noted, some embodiments can be implemented in which a single end of the scaffold is retained within an aperture or otherwise engaged by the elongate member.

Additionally, FIGS. 6A and 6C illustrate that the reduced cross-sectional segments 320, 322 can be positioned within the respective apertures 600, 602. For example, the reduced cross-sectional segments 320, 322 and the respective apertures 600, 602 can each have substantially equal lengths, measured in the direction transverse to an axis of the lumen 400. Thus, a given reduced cross-sectional segment can be seated or received into a respective aperture and achieve a fit with the aperture such that the respective proximal or distal section of the scaffold is generally restrained against movement or rotation in a direction 650 transverse to an axis of the lumen 400.

For example in some embodiments, the proximal and/or distal sections 310, 312 can comprise planar portions, as illustrated in discussed above with respect to FIG. 5. Additionally, the proximal and/or distal sections 310 can comprise an end or tab extending therefrom. The tabs can be formed at the distal ends of the proximal and distal sections 310, 312. The tabs can also be larger than the section of the proximal or distal section 310, 312 extending through the aperture 600, 602 (which can be the reduced cross-sectional segments 320, 322, in some embodiments).

For example, the tabs can be a portion of the proximal and distal sections 310, 312 that remains or exists in the presence of the reduced cross-sectional segments 320, 322. The tabs can protrude and create an interference against the outer surface of the catheter 210 in order to block or inhibit motion of the respective proximal or distal section 310, 312. For example, the tabs can be configured to extend out of the apertures 600, 602 and to abut an outer surface of the catheter 210, thereby generally restricting movement or rotation of the respective proximal or distal section of the scaffold in a direction 650 transverse to an axis of the lumen 400.

Accordingly, some embodiments can be configured such that the proximal and/or distal sections 310, 312 can be constrained against movement in an axial direction 646, a radial direction 648, and a transverse direction 650. Thus, when the implant 300 or scaffold 302 is coiled about the engagement section 216 of the catheter 210, the proximal and distal sections 310, 312 of the scaffold 302 can be secured in various directions to be engaged during delivery of the implant 300 to the treatment site. When the implant 300 reaches the treatment site, the implant 300 can then be expanded.

An initial phase of the implant expansion is illustrated in FIG. 6D. As shown, the proximal portion 310 of the scaffold 302 is engaged or retained by an elongate member 420. However, the scaffold 302 has expanded from a mounted or collapsed state (shown in FIG. 6B) to an expanded state (shown in FIG. 6D) because the distal section 312 of the scaffold 302 has been released from engagement with the catheter 210. When released, the stress in the wound scaffold 302 can be released as the implant distal section 312 unwinds (perhaps along with a portion of the scaffold 302 intermediate the distal and proximal sections 310, 312). For example, the distal and proximal sections 310, 312 can rotate or unwind relative to each other, allowing the diameter of the implant 300 to expand while it unwinds or rotates. The scaffold 302 can have fewer winds in the expanded position when the scaffold 302 has achieved a target diameter (likely configured to be slightly larger than the interior dimensions of the target vessel to allow the implant 300 to be urged into contact with the vessel wall). For example, in the expanded, unwound position, the scaffold 302 can have from about 4 to about 10 winds, from about 5 to about 8 winds, and in some embodiment about 6 or about 7 winds.

Thereafter, in order to fully release the scaffold 302, the engagement member 420 can be moved (either proximally or distally, depending on the configuration of the engagement member 420) in order to disengage from the proximal section 310 of the scaffold 302.

Figure 6E:
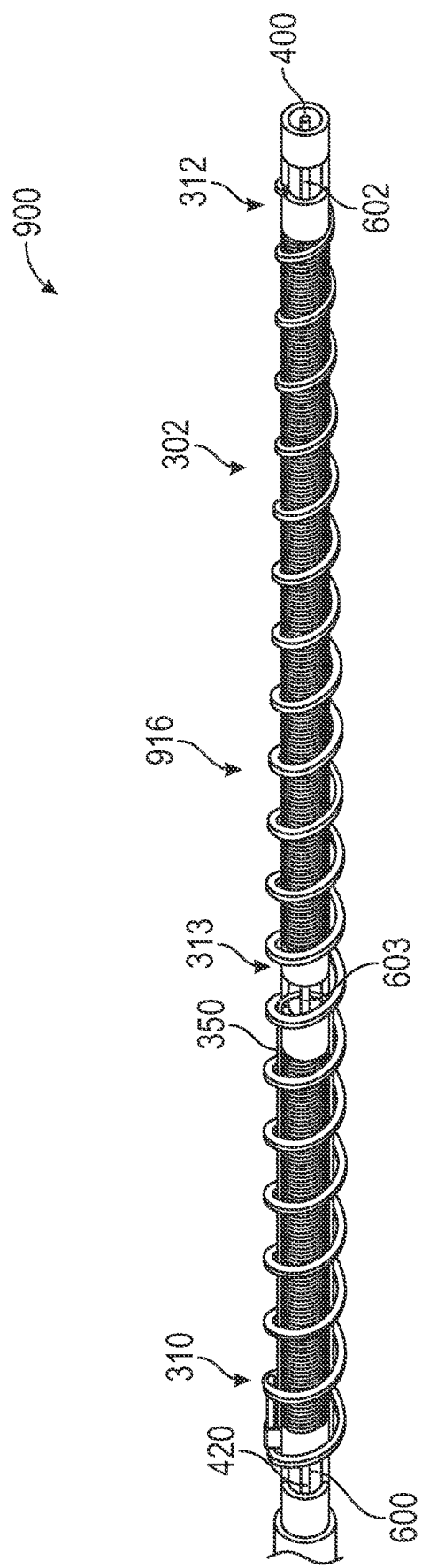

As shown in FIGS. 6E and 6F, in some embodiments, the implant carrier assembly 900 can engage a proximal section 310, a middle section 313, and/or a distal section 312 of the scaffold 302. Optionally, the implant carrier assembly 900 can engage the backbone support 350 at the middle section of the scaffold 302. Similar to other embodiments described herein, the implant carrier assembly 900 can also be configured to comprise at least one elongate member 420 that extends at least partially through the catheter lumen 400. The elongate member 420 can engage at least a portion of, and in some embodiments, one or more of the proximal, distal, and middle sections 310, 312, 313 of the scaffold 302.

As described with respect to other embodiments, the elongate member 420 can be selectively actuated or withdrawn in order to release engagement between the scaffold 302 in the elongate member 420. For example, the elongate member 420 can be moved a first distance (whether proximally or distally) in order to release or disengage with one of the proximal, distal or middle sections 310, 312, 313 of the scaffold 302. Further, the elongate member 420 can be moved a second distance, greater than the first distance (whether proximally or distally) in order to release or disengage with another of the proximal, distal, or middle sections 310, 312, 313 of the scaffold 302. In some embodiments, the elongate member 420 can be moved a third distance, greater than the first and second distance (whether proximally or distally) in order to release or disengage with the remaining of the proximal, distal, or middle sections 310, 312, 313 of the scaffold 302. Optionally, when the elongate member 320 is moved to the second distance, the remaining attached or coupled sections of the proximal, distal, and/or middle sections 310, 312, 313 of the scaffold 302 are released or disengaged.

Further, in some embodiments, the engagement section 916 can facilitate engagement between the implant 300 and two or more elongate members 420 extending from the handle assembly 250. Although the elongate member 420 is illustrated as extending between the proximal, distal, and middle sections 310, 312, 313 of the implant scaffold 302, the elongate member 420 can engage one of the proximal, distal, and middle sections 310, 312, 313 while a second elongate member can be used to engage another of the proximal, distal, and middle sections 310, 312, 313. In some embodiments, a third elongate member can be used to engage the other of the proximal, distal, and middle sections 310, 312, 313. Optionally, a single elongate member can engage one of the proximal, distal, and middle sections 310, 312, 313 while another elongate member engages more than one of the remaining proximal, distal, and middle sections 310, 312, 313.

In some embodiments, the catheter 210 can be configured to comprise a proximal aperture 600, a distal aperture 602, and a middle aperture 603. The proximal, distal, and middle aperture 600, 602, 603 are configured to extend through the wall 402 of the catheter 210. Further, the apertures 600, 602, 603 are configured as slots or notches that extend transversely relative to a longitudinal axis of the catheter lumen 400. The apertures 600, 602, 603 can extend radially at least partially into the lumen 400, and as illustrated, can extend about halfway across a diameter of the lumen 400. For example, as illustrated in FIG. 6E, some embodiments can be configured such that at least one of the proximal, distal, or middle sections 310, 312, 313 of the scaffold 302 extends within the respective proximal, distal, and middle aperture 600, 602, 603 of the catheter 210.

Further, FIG. 6E also illustrates the scaffold 302 of the implant 300 in a mounted, collapsed, or wound position. Thus, before the scaffold 302 or stent 300 is released, the scaffold 302 is helically wound tightly around the catheter 210. The winding of the scaffold 302 about the catheter distal portion can put the scaffold 302 into a stressed state. As discussed further below, the scaffold 302 will tend to rebound or expand from the stressed, mounted, collapsed, or wound position.

Accordingly, some embodiments can be configured such that the proximal, distal, and/or middle sections 310, 312, 313 can be constrained against movement in an axial direction, a radial direction, and a transverse direction. Thus, when the implant 300 or scaffold 302 is coiled about the engagement section 216 of the catheter 210, the proximal, distal, and/or middle sections 310, 312, 313 of the scaffold 302 can be secured in various directions to be engaged during delivery of the implant 300 to the treatment site. In some embodiments, engagement of the middle section 313, including, but not limited to the backbone support 350, of the scaffold 302 about the engagement section 916 can allow the scaffold to be mounted, collapsed, or wound with a reduced overall profile. When the implant 300 reaches the treatment site, the implant 300 can then be expanded.

An initial phase of the implant expansion is illustrated in FIG. 6F. As shown, the proximal section 310 and the middle section 313 (e.g. the support backbone 350) of the scaffold 302 are engaged or retained by an elongate member 420. However, the scaffold 302 has expanded from a mounted or collapsed state to an expanded state because the distal section 312 of the scaffold 302 has been released from engagement with the catheter 210. When released, the stress in the wound scaffold 302 can be released as the implant distal section 312 unwinds. For example, the distal and proximal sections 310, 312 can rotate or unwind relative to each other, allowing the diameter of the implant 300 to expand while it unwinds or rotates. The scaffold 302 can have fewer winds in the expanded position when the scaffold 302 has achieved a target diameter (likely configured to be slightly larger than the interior dimensions of the target vessel to allow the implant 300 to be urged into contact with the vessel wall). Thereafter, in order to fully release the scaffold 302, the engagement member 420 can be moved (either proximally or distally, depending on the configuration of the engagement member 420) in order to disengage from the proximal section 310 and the middle section 313 of the scaffold 302 (either concurrently or sequentially).

Figure 7A:
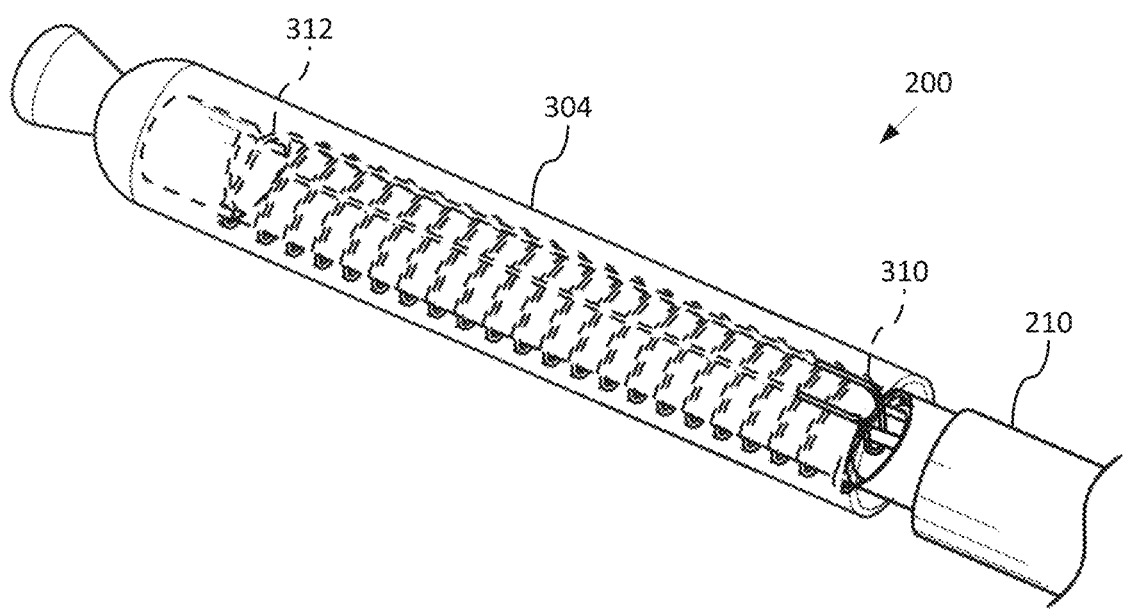
FIGS. 7A-7B illustrate perspective views of an occlusive implant, with a backbone support, in a mounted or collapsed position on a catheter, according to some embodiments.
Figure 7B:
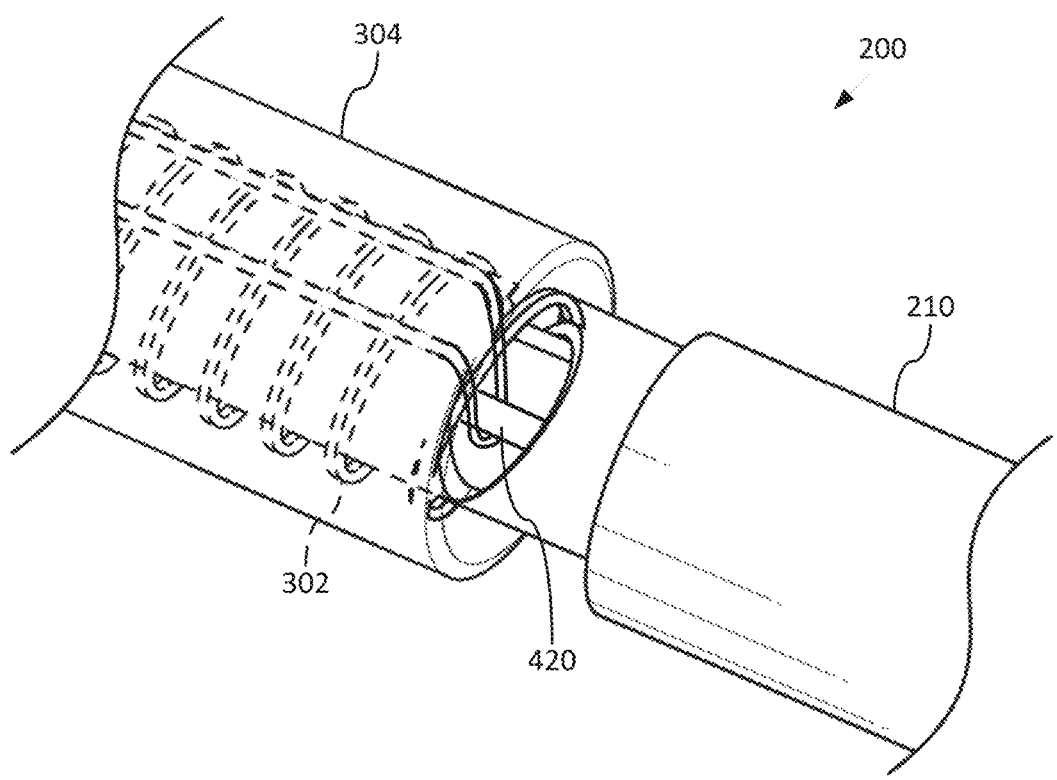

FIGS. 7A and 7B illustrate perspective views of the implant carrier assembly 200, similar to the illustrations of FIGS. 6A and 6B, but further including the implant membrane 304. As illustrated, the implant membrane can be positioned over the scaffold 302 and delivered in a mounted or collapsed state. The elongate member 420 can be engaged with the proximal section 310 of the scaffold 302. Further, as noted above, the elongate member 420 or a different elongate member can be engaged with the distal section 312 of the scaffold 302.

Figure 8A:
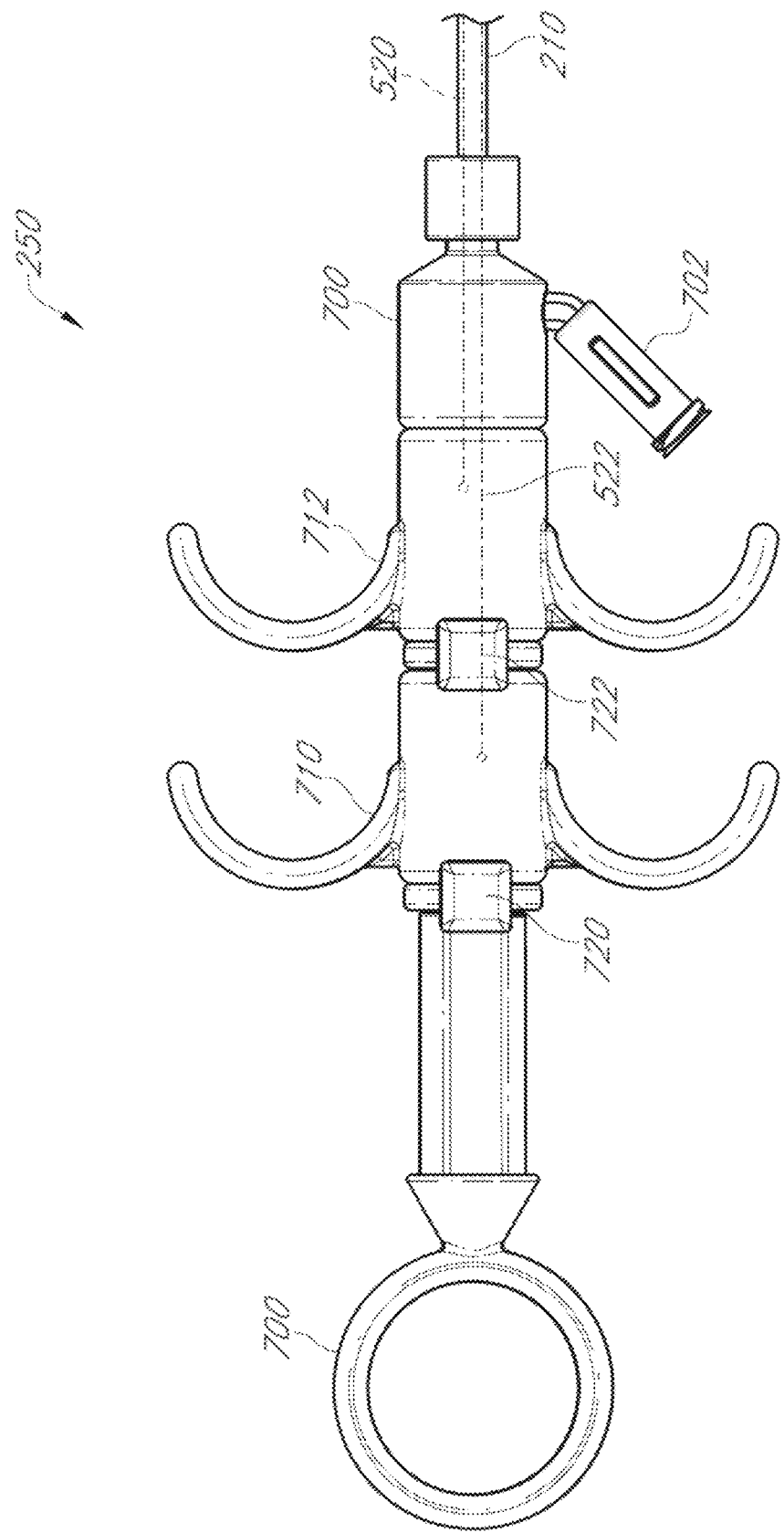
FIGS. 8A and 8B illustrate views of a handle assembly, according to some embodiments.

Referring now to FIG. 8A, the implant carrier assembly 200 can also comprise the handle assembly 250. The handle assembly 250 can be used to deploy the proximal and distal sections 310, 312 of the implant 300. In some embodiments, the assembly 250 can include a deployment handle or body 700 with a side port 702 to accommodate syringe attachment to flush the catheter 210 of air and to pre-expand the membrane 304 before deploying the implant 300.

The handle assembly 250 can also comprise at least one slider member configured to actuate an elongate member of the assembly 200. In the embodiment illustrated in FIG. 10, the handle assembly 250 can also be configured to comprise more than one slider member. As illustrated, the handle assembly 250 comprises first and second slider members 710, 712. The first and second slider members 710, 712 can be coupled to respective elongate members, such as elongate members 522, 520 of the embodiment illustrated in FIG. 6B.

Additionally, in accordance with some embodiments, the handle assembly 250 can also comprise one or more retention clips 720, 722. The retention clips 720, 722 can be configured to prevent movement of the slider members 710, 712 relative to the handle 700, thereby restricting movement of the elongate members 520, 522 and premature deployment of the implant. When the retention clips 720, 722 are removed, which may be done separately or together, the slider members 710, 712 can be used to release the proximal and distal ends of the implant. For example, the proximal slider member 710 can be configured to release the proximal end of the implant. Further, the distal slider member 712 can be configured to release the distal end of the implant.

Figure 8B:
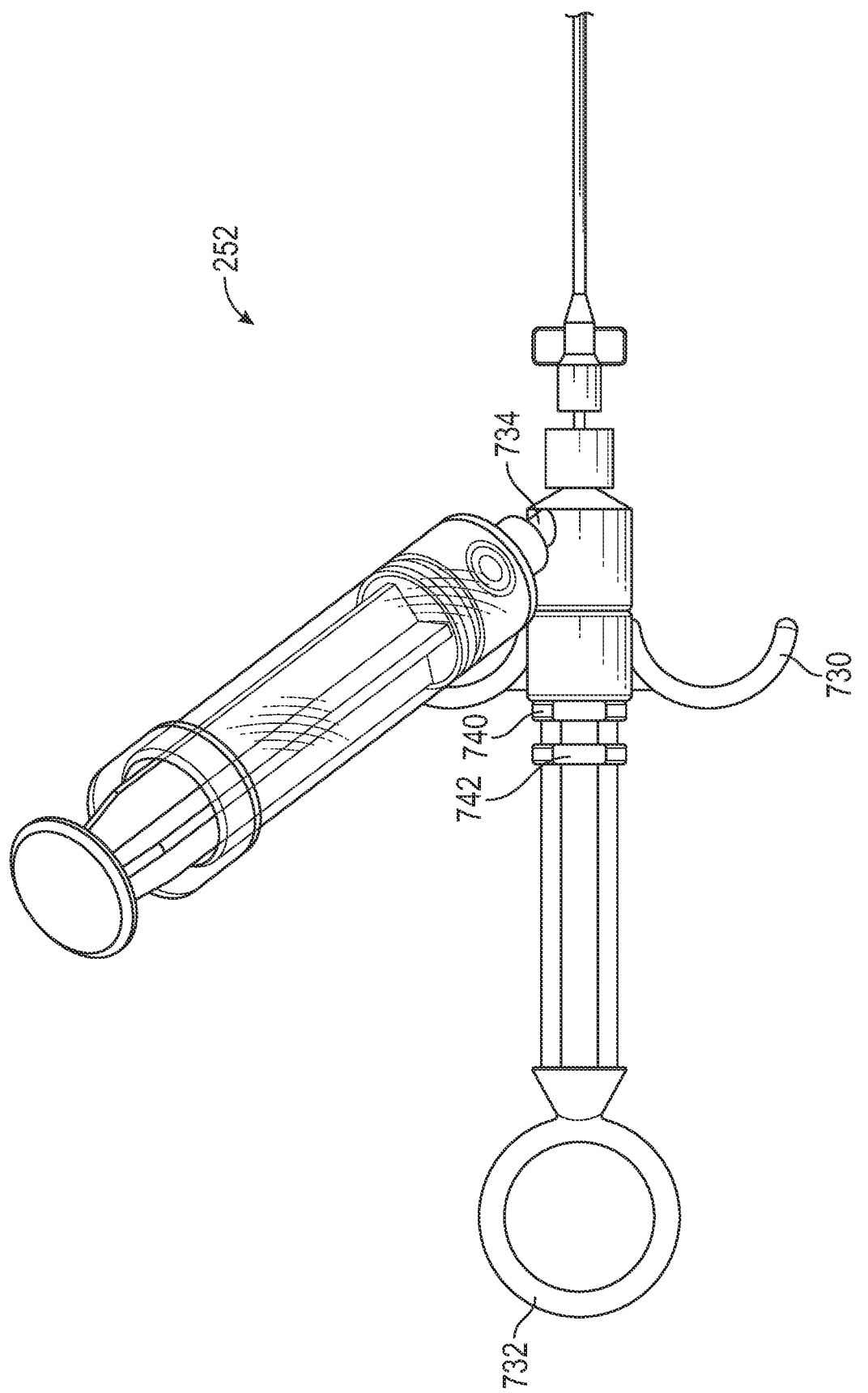
Figure 9A:
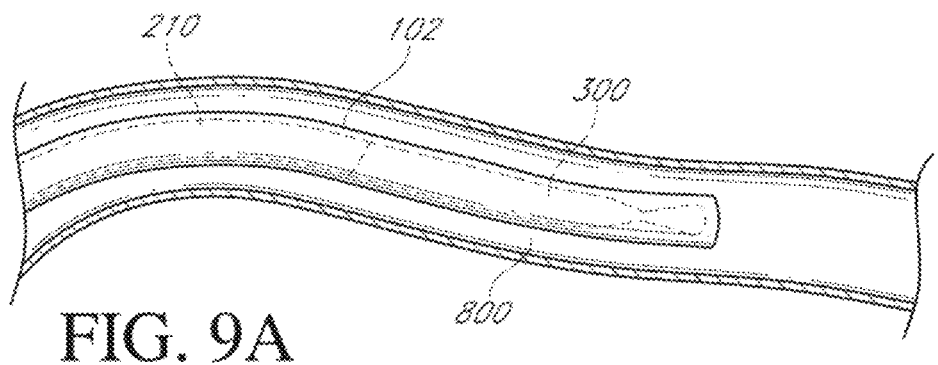
FIGS. 9A-9D illustrate sequential views of an expansion process of an occlusive implant with a backbone support, according to some embodiments.
Figure 9B:
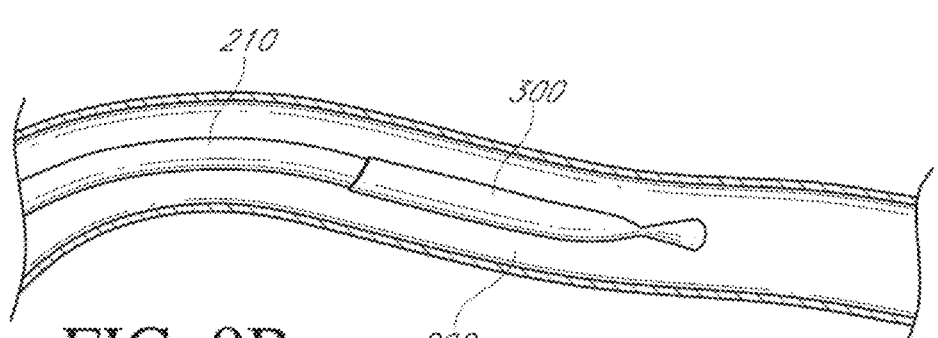
Figure 9C:
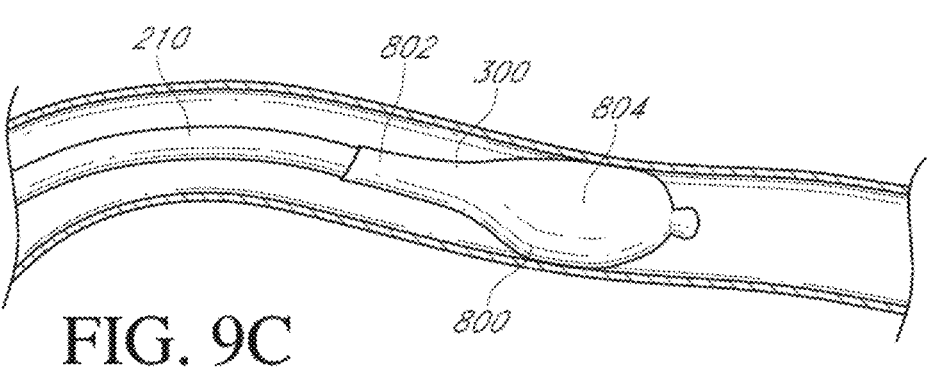
Figure 9D:
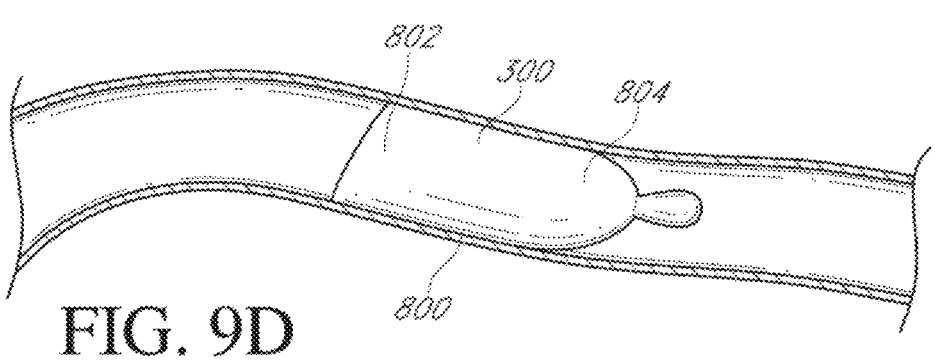

As shown in FIG. 8B, in some embodiments, the handle assembly 252 can also comprise a single slider member configured to actuate an elongate member of the assembly. As illustrated, an embodiment of a handle assembly 252 can comprise aslider member 730, a handle 732, and a side port 734. In the depicted example, the slider member 730 can be coupled to one or more elongate members.

Additionally, in accordance with some embodiments, the handle assembly 252 can also comprise retention clips 740, 742. The retention clips 740, 742 can be configured to prevent movement of the slider member 730 relative to the handle 700, thereby restricting movement of the elongate members and premature deployment of the implant. When the retention clips 740, 742 are removed, which may be done separately or together, the slider member 730 can be used to release the proximal, middle, and/or distal portions of the implant. For example, upon removal of the retention clip 740, the slider member 730 may be actuated to release the distal portion of the implant. Further, upon removal of the retention clip 742 (and the retention clip 740), the slider member 730 may be actuated to release the middle and/or the proximal portion of the implant.

Implant deployment can be performed as a two stage process, which is illustrated in FIGS. 9A-9D. The guide catheter 102 and implant can first be moved to a target location 800 (shown FIG. 9A). The guide catheter 102 can then be removed (shown in FIG. 9B). After the distal-most retention clip is removed from the handle assembly, the distal slider member of the handle assembly can be pulled proximally to release a distal end 804 of the implant 300 (shown in FIG. 9C). When the distal implant end 8804 is released, the physician can check the implant position and observe as the inner space of the implant 300 fills with blood. Some slight movement of the implant 300 may be helpful to achieve precise placement. The second retention clip of the handle assembly can then be removed and the proximal slider member of the handle assembly can be pulled proximally to release a proximal end 802 of the implant (shown in FIG. 9D), thus releasing the entire implant 300.

When the implant 300 is released into the target location 800, the scaffold 302 may expand without quite reaching the default expanded state. Thus, the scaffold 302, including the backbone support 350, may engage against the body lumen walls at the target location 800. As shown in FIGS. 9A-9D, the membrane 304 may conform to a shape of scaffold 302 as it expands.

In some implementations, a longitudinal length of scaffold 302 when released in target location 800 is at least a fraction of the longitudinal length of scaffold 302 in a default expanded state or configuration. For example, the fraction may correspond to no less than 70%, 80%, 90%, 95%, or another ratio below 100%.

In other implementations, a longitudinal length of scaffold 302 when released in target location 800 is at least a predefined distance from the longitudinal length of scaffold 302 in a default expanded state or configuration. For example, the longitudinal length may be shorter by at least a predefined distance from the expanded configuration.

In forming the frame or others disclosed herein, the individual wires can be shaped or heat set into a curvilinear configuration before and/or after being joined with a corresponding wire to create the respective frame configuration. The wires (whether coupled together to form the frame or individually) can comprise a metal or polymer material, and can be heat set, molded, or otherwise shaped to have a resilient, self-expanding, bistable, and/or expandable shape. The frames can be self-expandable or balloon expandable.

Although embodiments of the present disclosure include a frame having a cylindrical profile in an expanded configuration, some embodiments include a frame having other shape profiles. The frame may have a cross-sectional profile with a regular or irregular shape, such as a square, pentagon, hexagon, cross, triangle, or some other shape having concave or convex portions or sharp or rounded edges relative to a longitudinal axis. Further, instead of or in combination with the generally round or oval-shaped hoop structures disclosed herein, the shape of the frame can be employed in any of the implant embodiments disclosed herein.

Delivery Systems

In accordance with some embodiments, a delivery system is provided that can control release and expansion of the implant at a target site within a lumen of a vasculature. The delivery system may comprise an implant carrier assembly with an occlusive implant retained therein. The implant carrier assembly can be inserted into a lumen where the occlusive implant can be positioned. The occlusive implant can then be deployed and released from the implant carrier assembly and permitted to expand within the lumen. Examples of such delivery systems are described in, for example, U.S. patent application Ser. No. 15/476,873 (122270-5064).

Cover Component Features

As disclosed in U.S. patent application Ser. No. 15/476,873, filed on Mar. 31, 2017 (122270-5064), the entirety of each of which is incorporated herein by reference, in some embodiments, the implant can comprise at least one cover component, member, membrane, mesh, or patch to assist in occluding, partially or completely, a luminal structure in which a respective implant is deployed. A cover component may be attached to one or both ends or support elements of an implant and/or to a middle region of an implant. The cover component can be configured as those disclosed in copending U.S. patent application Ser. No. 14/628,096, filed on Feb. 20, 2015 (122270-5042), the entirety of which is incorporated herein by reference.

In some embodiments, the cover component may be attached to each hoop structure by using an ePTFE membrane and fusing two or more layers of the ePTFE together. In some embodiments, the ePTFE membrane can be an unsintered ePTFE. In some embodiments, the two or more layers of the ePTFE can be fused together by applying heat.

In accordance with some embodiments, including any of the implant structures disclosed herein, an implant can be provided in which one or more of the hoop members comprises a cover component, such as that discussed with respect to the ePTFE. For example, hoop members at the proximal and distal ends of the implant can comprise ePTFE membranes that can facilitate blockage of flow immediately upon release of the implant.

In some embodiments, a cover component can comprise at least one of a polyurethane, a polyanhidrate, PTFE, ePTFE, silicone, and other suitable materials known to those of ordinary skill in the art. In some embodiments, cover components may be elastic. In some embodiments, cover components may be permeable or non-permeable.

Some embodiments can be configured such that the cover component can carry biocompatible medications or materials, such as hydrogels, collagens, or embolic materials. Further, the implant can comprise a cover component that extends around and/or within the support frames in a variety of ways.

The cover component can comprise a mesh material that is attached to support elements of the frame of an implant. The cover component can be formed from a tubular material that extends around and encloses the support elements, and in some embodiments, the entire frame of an implant. However, the cover component can also be adhered or coupled to the support elements by themselves. In some embodiments, the cover component can comprise a single layer of material.

Additionally, some embodiments can be configured such that when released into a body lumen, the cover component can facilitate occlusion of the lumen through the use of hydrogels, collagens, adhesives, or other coatings that disrupt or reduce flow through the lumen of the implant.

In some embodiments, an average thickness of a cover component can be between about 0.0005 inches and about 0.006 inches. In some embodiments, the average thickness of a cover component may be less than about 0.0005 inches or greater than about 0.006 inches. In certain embodiments, an average thickness of a distal portion of a cover component is greater than an average thickness of a proximal portion of a cover component. Such a configuration may ensure that more flow may be reduced at the distal portion of a cover component.

In some embodiments, the average thickness of the distal portion of a cover component is between about 0.002 inches and about 0.012 inches. In some embodiments, the average thickness of the distal portion of a cover component may be less than about 0.002 inches or greater than about 0.012 inches. In some embodiments, the average thickness of the proximal portion of a cover component is between about 0.0005 inches and about 0.006 inches. In some embodiments, the average thickness of the proximal portion of a cover component may be less than about 0.0005 inches or greater than about 0.006 inches.

Valve Mechanisms

Some embodiments of the implant frame can comprise a valve mechanism that allows a portion of the implant frame to collapse, thus restricting flow through the implant, as disclosed in copending U.S. patent application Ser. No. 14/304,868, filed on Jun. 13, 2014 (122270-5035), the entirety of which is incorporated herein by reference. Further, in accordance with some embodiments, the valve mechanisms disclosed herein can be used in a manner suitable for deploying an embolic material to a target region, such as for cancer therapy, as disclosed in copending U.S. patent application Ser. No. 14/101,171, filed Dec. 9, 2013 (122270-5028), the entirety of which is incorporated herein by reference.

Implant Materials and Coatings

According to some embodiments of the subject technology, the support frame of the implant may comprise at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, support frame may comprise at least one of polyethylene, polyglicolide, polylactide, ε-caprolactone, polycarbonate, hydroxyalkanote, para dioxinine, polytetrafluoroethylene (PTFE), expanded polytetrafluoroethylene (ePTFE), PLA, PGA, PLLA, PDLLA, PDO, PCL, and other suitable materials known to those of ordinary skill in the art.

In some embodiments, support frame and/or occlusion membrane, may comprise a bioabsorbable material, beneficially allowing for their controlled degradation. In some embodiments, support frame and/or occlusion membrane may be formed of bioabsorbable material to have a controlled degradation anywhere between about 3 months to about 3 years depending on the desired application of support frame. In some embodiments, the controlled degradation may be less than about 3 months or greater than about 3 years. For example, hydrolysis of ester linkages or effects of enzymatic degradation may be utilized for the controlled degradation.

In some embodiments, components of the implants disclosed herein, including the frame, cover component, and/or occlusive components and/or materials, may be surface finished and/or coated with various suitable agents, such as hydrogels, collagens, drugs, adhesives, and the like, to facilitate expansion of the implant, facilitate engagement of the implant within the body lumen, and/or promote occlusion by the implant of the body lumen. For example, the support frame can be coated with a material to facilitate expansion within and engagement between the implant and the inner surface of the vessel or lumen. Further, the frame, cover component, and/or occlusive components and/or materials may be coated with biological glue, hydrogels, collagens, drugs, and/or adhesive materials. In some embodiments, support frame may be coated with a friction-resistant coating (e.g., a friction-resistant polymer coating). In some embodiments, radio-opaque markers may be located on support frame or occlusion membrane for endovascular or other image-guided procedures. In some embodiments, the radio-opaque marker may be a platinum iridium alloy or other suitable markers known to those of ordinary skill in the art.

Medical Applications and Procedures for Some Embodiments

The occlusive implants, catheters, systems, and methods can be used in a variety of clinical applications, such as rapid, well-controlled, and reliable temporary or permanent vessel occlusion, stenting, or other functions in luminal structures of a patient. According to some embodiments, the implants, catheters, systems, and methods disclosed herein can be used for percutaneous, peripheral occlusion of the arterial and venous vasculature. However, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, the implants, catheters, systems, and methods disclosed herein may be used for temporary occlusion in cases of lung disease, or for temporary occlusion of female reproductive organs for contraceptive purposes. In some embodiments, the implant(s) may be removed, or flow may be restored through the luminal structure to restore original organ functions.

Some embodiments of the occlusive implants, catheters, systems, and methods can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, or close an abnormal blood vessel or blood vessels supplying a vascular anomaly such as arteriovenous malformations or arteriovenous fistulas, and other conditions.

Further, some embodiments may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). Some embodiments may be used for stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). Some embodiments may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, and other such issues), and devascularization prior to (or as an alternative to) surgical resection of various organs or tumors.

Furthermore, some embodiments may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of uretero-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of the implants, catheters, systems, and methods disclosed herein is not limited to applications for human patients, but may also include veterinary applications.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 12, or clause 13. The other clauses can be presented in a similar manner.

Clause 1. An implant including: an expandable frame including a plurality of loops, the expandable frame including a first end portion and a second end portion; and a backbone support coupled to the second end portion of the expandable frame and extending from the second end portion towards the first end portion along an outer perimeter of the expandable frame.

Clause 2. The implant of Clause 1, wherein the implant includes a single wire that (i) extends from a coupling point at the second end portion of the expandable frame to form the plurality of loops, then (ii) reverses path to extend along the plurality of loops until returning to the coupling point at the second end portion, thereby forming a dual wire frame.

Clause 3. The implant of Clause 2, wherein upon returning to the coupling point at the second end portion, the wire extends continuously to form the backbone support, the wire extending from the second end portion toward a return point at the first end portion, whereat the wire reverses path to extend from the first end portion toward the second end portion thereby forming the backbone support.

Clause 4. The implant of any one of the previous Clauses, wherein the backbone support includes a U-shaped member.

Clause 5. The implant of any one of the previous Clauses, wherein the plurality of loops includes a plurality of windings of a coil Clause 6. The implant of any one of the previous Clauses, wherein the plurality of loops includes a helical member.

Clause 7. The implant of any one of the previous Clauses, wherein the expandable frame includes a series of loops.

Clause 8. The implant of any one of the previous Clauses, wherein the expandable frame includes a series of loops.

Clause 9. The implant of any one of the previous Clauses, wherein a handle portion is connected to a first end of the expandable frame.

Clause 10. The implant of Clause 9, wherein the handle portion includes a ring shape.

Clause 11. The implant of Clause 9, wherein the plurality of loops include a first loop at the first end of the expandable frame, and wherein a curvature of a portion of the first loop is smaller than a curvature of other loops in the plurality of loops.

Clause 12. An implant for placement in a body lumen, the implant including an expandable support frame that upon release from a delivery system moves from a collapsed configuration to an expanded configuration to permit the implant to expand within and restrain flow through the body lumen, the support frame including a first longitudinal length in the collapsed configuration and a second longitudinal length in the expanded configuration, the first longitudinal length being greater than the second longitudinal length, the support frame further including a backbone support having a backbone length that is approximately equal to the second longitudinal length, wherein the backbone is coupled to at least one of a first end portion or a second end portion of the support frame to permit the backbone support to provide tensile resistance against longitudinal expansion of the support frame, thereby facilitating engagement of the implant against a wall of the body lumen.

Clause 13. The implant of Clause 12, wherein the implant includes a single wire that (i) extends from a coupling point at the second end portion of the expandable frame to form the plurality of loops, then (ii) reverses path to extend along the plurality of loops until returning to the coupling point at the second end portion, thereby forming a dual wire frame.

Clause 14. The implant of Clause 13, wherein upon returning to the coupling point at the second end portion, the wire extends continuously to form the backbone support, the wire extending from the second end portion toward a return point at the first end portion, whereat the wire reverses path to extend from the first end portion toward the second end portion thereby forming the backbone support.

Clause 15. The implant of any one of Clauses 12-14, wherein the backbone support includes a U-shaped member.

Clause 16. The implant of any one of Clauses 12-14, wherein the plurality of loops includes a plurality of windings of a coil Clause 17. The implant of any one of Clauses 12-14, wherein the plurality of loops includes a helical member.

Clause 18. The implant of any one of Clauses 12-14, wherein the expandable frame includes a series of loops.

Clause 19. The implant of any one of Clauses 12-14, wherein the expandable frame includes a series of loops.

Clause 20. The implant of any one of Clauses 12-14, wherein a handle portion is connected to a first end of the expandable frame.

Clause 21. The implant of Clause 20, wherein the handle portion includes a ring shape.

Clause 22. The implant of Clause 20, wherein the plurality of loops include a first loop at the first end of the expandable frame, and wherein a curvature of a portion of the first loop is smaller than a curvature of other loops in the plurality of loops.

Clause 23. An implant for placement in a body lumen, the implant including: an expandable support frame having a first end portion and a second end portion; a tubular membrane extending along the expandable support frame for inhibiting flow through the support frame when the implant is positioned within a body lumen; and a backbone support coupled to the second end portion of the expandable support frame at a first end portion of the backbone support, the backbone support further having a free second end portion, the backbone support having a first longitudinal length that is no greater than a second longitudinal length of the expandable support frame when the expandable support frame is released into the body lumen.

Clause 24. The implant of Clause 23, wherein the expandable support frame has a third longitudinal length when the expandable support frame is allowed to expand to a default state, and wherein the second longitudinal length is no greater than the third longitudinal length at least in part due to engagement of the backbone support against a wall of the body lumen.

Clause 25. The implant of Clause 24, wherein the second longitudinal length is no less than 80% of the third longitudinal length.

Clause 26. The implant of any one of Clauses 23-25, wherein the second longitudinal length is no less than 90% of the third longitudinal length.

Clause 27. The implant of any one of Clauses 23-26, wherein the second longitudinal length is no less than 95% of the third longitudinal length.

Clause 28. The implant of any one of Clauses 23-27, wherein the tubular membrane conforms to a shape of the expandable support frame.

Clause 29. The implant of any one of Clauses 23-28, wherein in an expanded configuration, the free second end portion of the backbone support terminates in close proximity to the second end portion of the expandable support frame.

Clause 30. The implant of Clause 29, wherein close proximity is defined by a distance no greater than 5% of the first longitudinal length.

Clause 31. An assembly comprising any of the devices, implants, or components recited in any one of Clauses 1-30.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method clauses present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the Clauses, such term is intended to be inclusive in a manner similar to the term "comprise" as "comprise" is interpreted when employed as a transitional word in a Clause.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof.

What is claimed is:

1. An implant comprising:
an expandable frame comprising a plurality of loops, the expandable frame comprising a first end portion and a second end portion; and
a substantially straight backbone support coupled to the second end portion of the expandable frame at a coupling point and extending therefrom towards a return point at the first end portion whereat the backbone support reverses path to extend from the return point toward the coupling point along a majority of a longitudinal length of an outer perimeter of the expandable frame.

2. The implant of claim 1, wherein the implant comprises a single wire that (i) extends from the coupling point at the second end portion of the expandable frame to form the plurality of loops, then (ii) reverses path to extend along the plurality of loops until returning to the coupling point at the second end portion, thereby forming a dual wire frame.

3. The implant of claim 2, wherein upon returning to the coupling point at the second end portion, the wire extends continuously to form the backbone support.

4. The implant of claim 1, wherein the backbone support comprises a U-shaped member.

5. The implant of claim 1, wherein the plurality of loops comprises a helical member.

6. The implant of claim 1, wherein a handle portion is connected to a first end of the expandable frame.

7. The implant of claim 6, wherein the handle portion comprises a ring shape.

8. The implant of claim 6, wherein the plurality of loops includes a first loop at the first end of the expandable frame, and wherein a curvature of a portion of the first loop is smaller than a curvature of other loops in the plurality of loops.

9. The implant of claim 1, further comprising a membrane that is supported by the expandable frame.

10. An implant for placement in a body lumen, the implant comprising an expandable support frame made of a single wire that upon release from a delivery system moves from a collapsed configuration to an expanded configuration to permit the implant to expand within and restrain flow through the body lumen, the support frame comprising a first longitudinal length in the collapsed configuration and a second longitudinal length in the expanded configuration, the first longitudinal length being greater than the second longitudinal length, the support frame further comprising a generally straight backbone support extending longitudinally from one end of the support frame, doubling back, and extending a majority of the way back to the one end and having a backbone length that is approximately equal to the second longitudinal length, wherein the backbone support is coupled to at least one of a first end portion or a second end portion of the support frame to permit the backbone support to provide tensile resistance against longitudinal expansion of the support frame, thereby facilitating engagement of the implant against a wall of the body lumen.

11. An implant frame comprising:
a body having a first end portion, a second end portion, and a plurality of loops extending between the first and second end portions; and
a backbone support having (i) a base portion that is directly connected to the body second end portion and (ii) a substantially straight section comprising a wire extending along a majority of a longitudinal length of the implant frame from the base portion along the plurality of loops in a direction toward the body first end portion and bending to extend along a majority of a longitudinal length of the implant frame in a reverse path toward the base portion.

12. The implant frame of claim 11, wherein the backbone support comprises a free end portion that is positioned adjacent to the body first end portion.

13. The implant frame of claim 11, wherein the substantially straight section extends external to the plurality of loops.

14. The implant frame of claim 11, wherein the body and backbone support are formed from a single wire.

15. The implant frame of claim 11, further comprising a membrane that is supported by the frame.

16. The implant frame of claim 15, wherein the membrane is substantially impermeable.

17. An implant comprising a helical frame having first and second end portions, a membrane that covers the frame, and a straight backbone that (i) is directly connected to the first end portion and (ii) extends a majority of the length of the frame toward the second end portion, bends, and extends a majority of the length of the frame back towards the first end portion for enhancing implant stability.

18. The implant of claim 17, wherein the backbone comprises a single wire that extends from the first end portion toward the second end portion.

19. The implant of claim 18, wherein the single wire is bent adjacent to the second end portion to reverse path toward the first end portion.

20. The implant of claim 17, wherein the frame and backbone are formed from a single wire.

21. The implant of claim 17, wherein in an expanded configuration, the backbone has a length that is approximately equal to a length of the implant.

* * * * *